US007575766B2

(12) United States Patent
Hauptmann et al.

(10) Patent No.: US 7,575,766 B2
(45) Date of Patent: *Aug. 18, 2009

(54) TAGETES ERECTA WITH ALTERED CAROTENOID COMPOSITIONS AND RATIOS

(75) Inventors: Randal Hauptmann, Oswego, IL (US); Blair L. Winner, Ventura, CA (US); Alan Blowers, St. Charles, IL (US)

(73) Assignee: Ball Horticultural Company, West Chicago (*) Notice: Subject to any disclaimer, the term of this patent is extended or adjusted under 35 U.S.C. 154(b) by 0 days.

This patent is subject to a terminal disclaimer.

(21) Appl. No.: 10/447,769

(22) Filed: May 29, 2003

(65) Prior Publication Data

US 2004/0010826 A1   Jan. 15, 2004

Related U.S. Application Data

(63) Continuation-in-part of application No. 10/325,265, filed on Dec. 19, 2002, now Pat. No. 7,033,622, which is a continuation-in-part of application No. 10/180,775, filed on Jun. 26, 2002, now Pat. No. 6,784,351.

(60) Provisional application No. 60/302,460, filed on Jun. 29, 2001.

(51) Int. Cl.
A61K 36/28 (2006.01)
A23L 1/27 (2006.01)

(52) U.S. Cl. .................. 424/764; 424/725; 424/778; 424/774; 426/540; 800/323

(58) Field of Classification Search .............. 800/323; 426/615, 540; Plt./263; 424/764, 725, 778, 424/774
See application file for complete search history.

(56) References Cited

U.S. PATENT DOCUMENTS

| | | | |
|---|---|---|---|
| 2,918,370 A | 12/1959 | Helgren | |
| 4,670,247 A | 6/1987 | Scialpi | |
| 5,043,170 A | 8/1991 | Borenstein et al. | |
| 5,258,189 A | 11/1993 | Efstathiou | |
| 5,270,063 A | 12/1993 | Wullschleger et al. | |
| 5,290,605 A | 3/1994 | Shapira | |
| 5,308,759 A | 5/1994 | Gierhart | |
| 5,382,714 A | 1/1995 | Khachik | |
| 5,427,783 A | 6/1995 | Gierhart | |
| 5,523,494 A | 6/1996 | Torres-Cardona et al. | |
| 5,536,504 A | 7/1996 | Eugster et al. | |
| 5,605,699 A | 2/1997 | Bernhard et al. | |
| 5,618,988 A | 4/1997 | Hauptmann et al. | |
| 5,648,564 A | 7/1997 | Ausich et al. | |
| 5,684,238 A | 11/1997 | Ausich et al. | |
| 5,695,794 A | 12/1997 | Stark et al. | |
| 5,747,544 A | 5/1998 | Garnett et al. | |
| 5,811,273 A | 9/1998 | Misawa et al. | |
| 5,827,652 A | 10/1998 | Garnett et al. | |
| 5,849,345 A | 12/1998 | Giger et al. | |
| 5,854,015 A | 12/1998 | Garnett et al. | |
| 5,858,700 A | 1/1999 | Ausich et al. | |
| 5,910,433 A | 6/1999 | Kajiwara et al. | |
| 5,935,624 A | 8/1999 | DeLuca et al. | |
| 5,955,102 A | 9/1999 | Gorenbein et al. | |
| 5,965,795 A | 10/1999 | Hirschberg et al. | |
| 5,972,690 A | 10/1999 | Misawa et al. | |
| 6,056,962 A | 5/2000 | Kesharlal et al. | |
| 6,150,130 A | 11/2000 | Misawa et al. | |
| 6,191,293 B1 | 2/2001 | Levy | |
| 6,218,436 B1 | 4/2001 | Howard et al. | |
| 6,224,876 B1 | 5/2001 | Kesharlal et al. | |
| 6,232,530 B1 * | 5/2001 | DellaPenna et al. ......... 800/282 |
| 6,254,898 B1 | 7/2001 | Bragaglia | |
| 6,262,284 B1 | 7/2001 | Khachik | |
| 6,329,432 B2 | 12/2001 | Howard et al. | |
| RE38,009 E | 2/2003 | Garnett et al. | |
| 6,894,208 B2 * | 5/2005 | Winner .................... 800/323.1 |
| 2004/0022881 A1 | 2/2004 | Hauptmann et al. | |

FOREIGN PATENT DOCUMENTS

| | | |
|---|---|---|
| DE | 4020874 | 1/1991 |
| WO | WO91/03571 | 3/1991 |
| WO | WO92/16635 | 10/1992 |
| WO | WO96/40092 | 12/1996 |
| WO | WO99/61652 | 12/1999 |
| WO | WO 00/32788 | * 6/2000 |

OTHER PUBLICATIONS

Heslot, H. 1966. Mutation induction by physical and chemical mutagenic agents. Mutat. Plant. Breed., Proc. Panel, pp. 139-149.*

(Continued)

Primary Examiner—June Hwu
(74) Attorney, Agent, or Firm—Husch Blackwell Sanders Welsh & Katz

(57) ABSTRACT

A marigold plant, a regenerable portion thereof and seed are disclosed whose flower petals, leaves or flower petals and leaves contain one or more of an enhanced neoxanthin plus violaxanthin ratio, an enhanced β-carotene ratio, an enhanced lycopene ratio, an enhanced α-cryptoxanthin ratio, an enhanced phytoene ratio or an enhanced phytofluene ratio relative to that ratio in a non-mutant marigold. A marigold plant, a regenerable portion thereof and seed are also disclosed whose flower petals contain zeaxanthin esters and are substantially free of esters of both neoxanthin and violaxanthin, and wherein zeaxanthin constitutes at least about one-half of the extractable carotenoids when xanthophylls are assayed as alcohols. Also disclosed are methods of preparing such plants, oleoresins and comestible materials that have such carotenoid ratios.

34 Claims, 1 Drawing Sheet

OTHER PUBLICATIONS

Lewin, B. 1985. Genes. John Wiley & Sons. 2nd ed. p. 45.*

Medina et al. Marigold Flower Meal as a Source of an Emulsifying Gum. [online], [retrieved on Dec. 1, 2004]. Retrieved from the Internet <http://www.hort.purdue.edu/newcrop/proceedings1993/v2-389.html>.*

*Hortus Third A Concise Dictionary of Plants Cultivated in the United States and Canada*, MacMillan Publishing Company (1976).

W.I. Marusich et al., "Zeaxanthin as a Broiler Pigmeter", *Poultry Sci.*, 55:1486-1494 (1980).

Cetl et al, "Genetic and Cytogenetic Problems of *Tagetes* L. Breeding", *Folia Fac. Sci. Nat. Univ. Purkynianae Brun. Biol.*, 21(1):5-56 (1985).

Bone et al., "Preliminary Identification of the Human Macular Pigment", *Vision Res.*, 25(11):1531-1535 (1985).

Jyonouchi et al., "Studies of Immunomodulating Actions of Carotenoids. I. Effects of β-Carotene and Astaxanthin on Murine Lymphocyte Functions and Cell Surface Marker Expression in *In Vitro* Culture System", *Nutrition and Cancer*, 16(2):93-105 (1991).

Diaconu, "Utilization of Induced Variation in Breeding Pot Marigolds", *Agronomie*, 34(1):17-21 (1991).

Zaharia, et al., "Actiunea Radiathlor Gamma Asupra Germinatiei Si Biosintezei Pigmentilor Asimilatori Oa Unele Plante Floricole", *Seria Agricultura*, 44(1):107-114 (1991).

Tyczkowski et al., "Research Note: Preparation of Purified Lutein and Its Diesters from Extracts of Marigold (*Tagetes erecta*)", *Poultry Sci.*, 70(3):651-654 (1991).

Quackenbush et al., "Vitamins and Other Nutrients: Composition and Analysis of the Carotenoids in Marigold Petals", *J. Assoc. Off. Anal. Chem.*, 55(3):617-621 (1972).

Geetha et al., "Induced Chlorophyll and Viable Mutations in Tagetes Patula L.", *Acta Botanica Indica*, 20(2):312-314 (1992).

Khachik et al., "Separation and Identification of Carotenoids and Their Oxidation Products in the Extracts of Human Plasma", *Anal. Chem.*, 64:2111-2122.

Jyonouchi et al., "Studies of Immunomodulating Actions of Carotenoids. II. Astaxanthin Enhances *In Vitro* Antibody Production to T-Dependent Antigens Without Facilitating Polyclonal B-Cell Activation", *Nutrition and Cancer*, 19(3):269-280 (1993).

Fray et al., "Identification and Genetic Analysis of Normal and Mutant Phytoene Synthase Genes of Tomato by Sequencing, Complementation and Co-Suppression", *Plant. Mol. Biol.*, 22:589-602 (1993).

Bone et al., "Stereochemistry of the Human Macular Carotenoids", *Invest. Ophthalmol. Vis. Sci.*, 34(6):2033-2040 (1993).

Finnegan et al., "Transgene Inactivation: Plants Fight Back!", *Bio/Technology*, 12:883-888 (1994).

Tanaka et al., "Chemoprevention of Mouse Urinary Bladder Carcinogenesis by the Naturally Occurring Carotenoid Astaxanthin", *Carcinogenesis*, 15(1):15-19 (1994).

Seddon et al., "Dietary Carotenoids, Vitamins A, C, and E, and Advanced Age-Related Macular Degeneration", *JAMA*, 272(18):1413-1420 (1994).

Morris et al., "Serum Carotenoids and Coronary Heart Disease: The Lipid Research Clinics Coronary Primary Prevention Trial and Follow-Up Study", *JAMA*, 272(18):1439-1441 (1994).

Khachik et al., "Lutein, Lycopene, and Their Oxidative Metabolites in Chemoprevention of Cancer", *J. Cellular Biochem.*, 22:236-246 (1995).

Balnave et al., "Relative Efficiencies of Yellow Carotenoids for Egg Yolk Pigmentation", *AJAS*, 9(5):515-517 (1996)

Pogson et al., "Arabidopsis Carotenoid Mutants Demonstrate that Lutein is Not Essential for Photosynthesis in Higher Plants", *Plant Cell*, 8:1627-1639 (1996).

Bone et al., "Distribution of Lutein and Zeaxanthin Stereoisomers in the Human Retina", *Exp. Eye. Res.*, 64 (2):211-218 (1997).

Khachik et al., "Identification, Quantification, and Relative Concentrations of Carotenoids and Their Metabolites in Human Milk and Serum", *Anal. Chem.*, 69:1873-1881.

Piccaglia et al., "Lutein and Lutein Ester Content in Different Types of Tagetes Patula and T. Erecta", *Ind. Crops and Prod.*, 8:45-51 (1998).

Moehs, et al., "Analysis of Carotenoid Biosynthesis Gene Expression During Marigold Petal Development", *Plant Mol. Biol.*, 45:281-293 (2001).

Bernstein et al., "Identification and Quantitation of Carotenoids and Their Metabolites in the Tissues of the Human Eye", *Exp. Eye Res.*, 72:215-223 (2001).

AOAC 1984, *Official Methods of Analysis* (14th Ed.), the Association of Official Analytical Chemists, Arlington, VA, USA.

Bone et al., "Analysis of the Macular Pigment by HPLC: Retinal Distribution and Age Study", *Invest. Ophthalmol. Vis. Sci.*, 29(6):843-849 (1988).

Giovannucci et al., "Intake of Carotenoids and Retinol in Relation to Risk of Prostate Cancer", *J. Nat. Cancer Inst.*, 87(23):1767-1776 (1995).

Datta, et al., "Short Communication: Gamma Ray-Induced Genetic Manipulations in Flower Colour and Shape in *Dendranthema Grandiflorum* and Their Management Through Tissue Culture", *Plant Breeding*. 120:91-92 (2001).

Masakazu et al., "The Effects of Irradiating Gladiolus (Gladiolus X Grandiflora Hort.) Cormels with Gamma Rays on Callus Formation, Somatic Embryogenesis and Flower Color Variations in the Regenerated Plants", *J. Japanese Soc. Of Hort. Sci.*, 70(1):126-128 (2001).

Venkatachalam et al., "Effect of Gamma Rays on Some Qualitative and Quantitative Characters in Zinnia Elegans Jacq.", *Ind. J. Gen. & Plant Breeding*, 57(3):255-261 (1997).

Li et al., "A Fast Neutron Deletion Mutagenesis-Based Reverse Genetics System for Plants", *Plant Journal*, 27(3):235-242 (2001).

Love et al., "The Induction of Bud Sports in Coleus Blumei by Fast Neutrons", *Amer. Soc. Hort. Sci.*, 88:627-630 (1966).

Abe et al., *In Vitro Cell. & Dev. Bio.*, 38:93A (2002), Abstract P-1283.

Meyer et al., "Differences in DNA-Methylation are Associated With a Paramutation Phenomenon in Transgenic Petunia", *Plant Journal*, 4(1):89-100 (1993).

Napoli et al., "Introduction of a Chimeric Chalcone Synthase Gene into Petunia Results in Reversible Co-Suppression of Homologous Genes *in trans*", *Plant Cell*, 2:279-289 (1990).

Jorgensen et al., "Chalcone Synthase Cosuppression Phenotypes in Petunia Flowers: Comparison of Sense vs. Antisense Constructs and Single-Copy vs. Complex T-DNA Sequences", *Plant Mol. Biol.*, 31:957-973 (1996).

Hamilton et al., "A Species of Small Antisense RNA in Post-transcriptional Gene Silencing in Plants", *Science*, 286:950-952 (1999).

Metzlaff et al., "RNA-Mediated RNA Degradation and Chalcone Synthase A Silencing in Petunia", *Cell*, 88:845-854 (1997).

Chuang et al., "Specific and Heritable Genetic Interference by Double-Stranded RNA in *Arabidopsis thaliana*", *PNAS*, 97(9):4985-4990.

Wesley et al., "Construct Design for Efficient, Effective and High-Throughput Gene Silencing in Plants", *Plant Journal*, 27(6):581-590 (2001).

Yang et al., "Ribozyme-Mediated High Resistance Against Potato Spindle Tuber Viroid in Transgenic Potatoes", *Proc. Natl. Acad. Sci.*, 94:4861-4865 (1997).

Miki et al., "Procedures for Introducing Foreign DNA into Plants", in *Methods in Plant Molecular Biology and Biotechnology*, Glick et al., Eds., CRC Press, Boca Raton, Florida, pp. 67-88 (1993).

Klein et al., "Transformation of Microbes, Plants and Animals by Particle Bombardment", *Bio/Technology*, 10:286-291 (1992).

Horsch et al., "A Simple and General Method for Transferring Genes into Plants", *Science*, 227:1229-1231 (1985).

Gruber et al., "Vectors for Plant Transformation", in *Methods in Plant Molecular Biology an Biotechnology*, Glick et al., Eds., CRC Press, Boca Raton, Florida, pp. 89-119 (1993).

Moloney et al., "High Efficiency Transfromation of *Brassica Napus* Using *Agrobacterium* Vectors", *Plant Cell Reports*, 8:238-242 (1989).

Lotan, et al., "Cloning and Expression in *Escherichia coli* of the Gene Encoding β-C-4-Oxygenase, that Converts β-Carotene to the Ketocarotenoid Canthaxanthin in *Haematococcus Pluvialis*", *FEBS Letters*, 364:125-128 (1995).

Fraser, et al., "Enzymic Confirmation of Reactions Involved in Routes to Astaxanthin Formation, Elucidated Using a Direct Substrate in Vitro Assay", *Eur. J. Biochem.*, 252:229-236 (1998).

Misawa et al., "Elucidation of the *Erwinia Uredovora* Carotenoid Biosynthetic Pathway by Functional Analysis Gene Products Expressed in *Escherichia Coli*", *J. Bacteriology*, 172(12):6704-6712 (1990).

Misawa et al., "Production of β-Carotene in Zymomonas Mobilis and Agrobacterium Tumefaciens by Introduction of the Biosynthesis Genes from Erwinia Uredova", *Applied and Environmental Microbiology*, 57(6):1847-1849 (1991).

(Abstract Only) Cirilli et al., Technica Molitoria (1975), 26(7), 79-82.

Georgeson Botanical Garden, GBG Note No. 14 (2002); [Google Search under "gbg note marigold".].

[Vernon-Carter et al., *J. Texture Studies*, 27:625-641 (1996)].

Delgado-Vargas et al., *J. Agric. Food Chem.*, 46:698-706 (1998).

Vishnevtsky et al., Carotenoid Sequestration in plants: The Role of Carotenoid-Associated Proteins, *Plant Physiol*, vol. 4, No. 6, pp. 232-235 (1999).

Ruban et al., "The Effects of Illumination on the Xanthophyll Composition of the Photosystem II Light-Harvesting Complexes of Spinach Thylakoid Membranes", *Plant Physiol.*, vol. 104, p. 227-234 (1994).

* cited by examiner

TAGETES ERECTA WITH ALTERED CAROTENOID COMPOSITIONS AND RATIOS

CROSS-REFERENCE TO RELATED APPLICATIONS

This is a continuation-in-part of application Ser. No. 10/325,265 filed on Dec. 19, 2002 U.S. Pat. No. 7,033,622, that was a continuation-in-part of application Ser. No. 10/180,775 that was filed on Jun. 26, 2002 now U.S. Pat. No. 6,784,351, that itself claimed priority of provisional application Ser. No. 60/302,460 that was filed on Jun. 29, 2001.

TECHNICAL FIELD

The present invention relates to a marigold plant that contains carotenoid pigments present at other than the usual ratios. The invention more particularly relates to a marigold plant, a regenerable portion thereof, a hybrid or later generation whose petals, leaves or both petals and leaves, contain an enhanced ratio of one or more carotenoid compounds relative to lutein, and also seed that produces such a marigold plant, an oleoresin produced from such flowers or leaves and comestible products made using zeaxanthin and lutein. The flower petals of such a contemplated marigold typically also contain a measurable amount of zeta-carotene, a compound not normally found in marigold flower petals.

BACKGROUND OF THE INVENTION

Numerous epidemiological studies in various populations have shown that consumption of substantial amounts of fruits and vegetables rich in carotenoids can reduce the risk of acquiring several types of cancers. As a result, scientists have been focusing on investigating the protective effect of carotenoids such as beta-(β-)carotene in prevention of cancer, cardiovascular and eye diseases. These studies have been carried out despite the fact that β-carotene is only one of the prominent carotenoids found in fruits and vegetables whose consumption has been associated with health benefits. The reasons for such focus can be attributed to the pro-vitamin A activity of β-carotene and the limited commercial availability of other prominent food carotenoids.

Among the 40 to 50 carotenoids that are available from the diet and may be absorbed, metabolized, or utilized by the human body, only 13 carotenoids and 12 of their stereoisomers are routinely found in human serum and milk. [See Khachik et al., *Anal. Chem.*, 69:1873–1881 (1997).] In addition, there are 8 carotenoid metabolites and one stereoisomer in human serum or plasma that result from a series of oxidation-reduction reactions of three dietary carotenoids: lutein, zeaxanthin and lycopene. These metabolites were first isolated and characterized by Khachik et al. [See Khachik et al., *Anal. Chem.*, 64:2111–2122 (1992).]

In another study, the ingestion of purified supplements of dietary (3R,3'R,6'R)-lutein and (3R,3'R)-zeaxanthin was shown to not only result in an increase in the blood levels of these compounds in humans, but also in an increase in the concentration of their oxidative metabolites in plasma. [See Khachik et al., *J. Cellular Biochem.*, 22: 236–246 (1995).] These findings provided preliminary evidence that carotenoids may function as antioxidants in disease prevention. In addition, these results also established the importance of non-vitamin A-active dietary carotenoids, particularly, lutein, zeaxanthin, and lycopene.

There is increasing evidence that the macular pigment carotenoids, lutein and zeaxanthin, may play an important role in the prevention of age-related macular degeneration (ARMD), cataract formation, and other light-induced oxidative eye damage. In 1985 and 1993, Bone et al. demonstrated that the human macular pigment is a combination of lutein and zeaxanthin, and speculated that these dietary carotenoids may play a role in the prevention of an eye disease ARMD. [See Bone et al., *Vision Research*, 25:1531–1535 (1985) and Bone et al., *Invest. Ophthalmol. Vis. Sci.*, 34: 2033–2040 (1993).] Further work in a case-controlled epidemiological study in which the high consumption of fruits and vegetables, rich specifically in lutein and zeaxanthin was correlated to a 43 percent lower risk of ARMD later confirmed that speculation. [See Seddon et al., *J. A. Med. Assoc.*, 272(18) 1413–1420 (1994).] It has also been reported that an increased level of serum carotenoids other than β-carotene is associated with a lower incidence of heart disease. [See Morris et al., *J. Amer. Med. Assoc.*, 272(18):1439–1441 (1994).]

Bernstein et al. identified and quantified the dietary carotenoids and their oxidative metabolites in all tissues of the human eye and reported that nearly all ocular structures examined with the exception of vitreous, cornea and sclera had quantifiable levels of dietary (3R,3'R,6'R)-lutein, zeaxanthin, their geometrical (E/Z) isomers, as well as their metabolites, (3R, 3'S,6'R)-lutein (3'-epilutein) and 3-hydroxy-beta,epsilon-caroten-3'-one. In the iris, these pigments were thought likely to play a role in filtering phototoxic short-wavelength visible light and to act as antioxidant in the ciliary body. Both mechanisms may be operative in the retinal pigment epithelium/choroid (RPE/choroids). [See Bernstein et al., *Exp. Eye Research*, 72(3):215–223 (2001).]

A study of the distribution of macular pigment stereoisomers in the human retina identified (3S,3'S)-zeaxanthin in the adult retina, particularly in the macula. It was proposed that dietary lutein and zeaxanthin are transported into an individual's retina in the same proportions found in the blood serum, although the two pigments are present in the eye in ratios different from those found in the blood. Thus, zeaxanthin predominates over lutein by a ratio greater than 2:1 in the foveal region, with the macular pigment optical density dropping by a factor of 100 and the zeaxanthin to lutein ratio reversing to about 1:2. [See Bone et al., *Invest. Ophthalmol. Vis. Sci.*, 29:843–849(1988).] Some lutein is converted into the non-dietary meso-zeaxanthin primarily in the macula. [See Bone et al., *Exp. Eye Res.*, 64(2): 211–218 (1997).] Such reports lend support to the critical role of ocular carotenoids, and therefore to the importance of commercial production of dietary carotenoids in general, and particularly lutein and zeaxanthin.

The *Tagetes* genus is a member of the family Compositae, alternatively known as Asteraceae, and comprises some thirty species of strongly scented annual or perennial herbs. *Tagetes* are native from Arizona and New Mexico to Argentina. [See *Hortus Third A Concise Dictionary of Plants Cultivated in the United States and Canada*, MacMillan Publishing Company (1976).] Cultivated genera include *Tagetes erecta*, commonly referred to as African marigold, *Tagetes patula*, commonly referred to as French marigold, *Tagetes erecta×patula*, commonly referred to as Triploid marigolds, and *Tagetes tenuifolia* also known as *Tagetes signata* or signet marigold.

A marigold inflorescence is a solitary head comprised of a dense cluster of several hundred sessile or subsessile small flowers also known as florets. Marigolds have radiate flower heads with outer ray florets that are ligulate or strap-shaped around the central tubular shaped disk florets. Some forms of marigold flower heads have most of their disk flowers transformed into ray flowers and contain few, if any, disk flowers. Such flower heads are referred to as double-flowered.

The ray flowers or florets are often referred to as petals by lay persons who may also refer to the flower heads as flowers. For ease of understanding, marigold flower heads will be referred to herein as flowers or flower heads, whereas the flower head-component flowers or florets, stamens, stigmas and carpels will be referred to as petals.

Cultivated marigolds possess showy flowers and are useful for ornamental purposes. In addition, the genus is recognized as a source for natural colorants, essential oils, and thiophenes. Dried marigold petals and marigold petal concentrates obtained from so-called xanthophyll marigolds are used as feed additives in the poultry industry to intensify the yellow color of egg yolks and broiler skin. [See Piccalia et al., *Ind. Crops and Prod.*, 8:45–51 (1998).] The carotenoids desired in poultry tissues are a function of their dietary concentration, because poultry do not have the ability to synthesize carotenoids de novo. [See Balnave et al., *Asian-Australiasian J. Animal Sci.*, 9(5):515–517 (1996).]

Xanthophyll marigolds differ in several characteristics from ornamental marigolds. First and foremost, xanthophyll marigolds are used as an extractable source for carotenoids and have plant habits that differ from ornamental marigolds. Ornamental marigolds typically grow only about 45 to about 60 cm from the ground, whereas xanthophyll marigolds grow to about 65 to about 70 cm from the ground. Xanthophyll marigolds grow in a bushier habit than do ornamental marigolds, and can be grown as row crops whereas ornamental marigolds typically cannot. Xanthophyll marigolds are typically dark orange in color, whereas ornamentals can be white, yellow, or orange in color, or can have mixed colors, including mahogany colors due to the presence of anthocyanin pigments.

The pigmenting ability of marigold petal meal resides largely in the oxygenated carotenoid fraction known as the xanthophylls, primarily lutein esters. [See Piccalia et al., *Ind. Crops and Prod.*, 8:45–51 (1998).] The xanthophyll zeaxanthin, also found in marigold petals, has been shown to be effective as a broiler pigmenter, producing a highly acceptable yellow to yellow-orange color. [See Marusich et al., *Poultry Sci.*, 55:1486–1494 (1976).] Of the xanthophylls, the pigments lutein and zeaxanthin are the most abundant in commercially available hybrids. Structural formulas for lutein and zeaxanthin are shown below.

Each of lutein and zeaxanthin contains one hydroxyl group in each of their terminal ring structures, so that each molecule contains two hydroxyl groups. Lutein is believed to be biologically produced by two separate hydroxylations of α-carotene, whereas zeaxanthin is believed to be biologically produced by two separate hydroxylations of β-carotene.

Both α-carotene and β-carotene are understood to be formed by the action of appropriate cyclase enzymes on lycopene to first yield δ-carotene or γ-carotene that thereafter cyclize further to form α-carotene or β-carotene, respectively. Lycopene, γ-carotene, α-carotene and β-carotene are each hydrocarbon carotenoids that are referred to in the art as carotenes. Thus, carotenoid pigments can be grouped into one or the other of two families: the hydrocarbon carotenes or the oxygenated xanthophylls. Phytoene, the first $C_{40}$ carotenoid in the pathway, is a colorless hydrocarbon. The hydrocarbon carotene pigments with the exception of β-carotene typically do not accumulate in marigold leaves or flower parts, whereas the xanthophylls do accumulate in both leaves and flower parts.

FIG. 1 shows a schematic representation of the biological synthesis pathway for the production of lutein and zeaxanthin and later products from phytoene via lycopene, γ-carotene, α-carotene and β-carotene. Lutein and zeaxanthin are present in marigold petals primarily as mono- and di-esters of fatty acids. FIG. 1 also notes epoxide-containing later products that can arise from zeaxanthin, of which violaxanthin is an intermediate in the abscisic acid biosynthetic pathway.

For the feed additive industry, xanthophyll marigolds are produced primarily in Mexico, Peru, Africa, India, China and Thailand. Modern, commercial varieties include 'Orangeade', one of the original xanthophyll producing varieties, and commercial improvements of 'Orangeade', including 'Deep Orangeade' having larger flowers and greater pigment yields, and 'Scarletade' an improvement for xanthophyll concentration. Thus, 'Orangeade' is reported to contain xanthophylls at about 9–12 mg/g of dry whole flower heads (including calyx), 'Deep Orangeade' is reported to have about 10–13 mg/g of those pigments, and 'Scarletade' is said to contain about 12–18 mg/g of xanthophyll pigments in dry flower heads weighed with the calyx. These varieties are available from PanAmerican Seed Co., 622 Town Road, West Chicago, Ill. 60185.

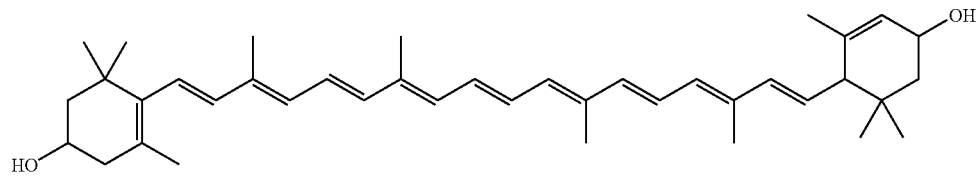

Lutein

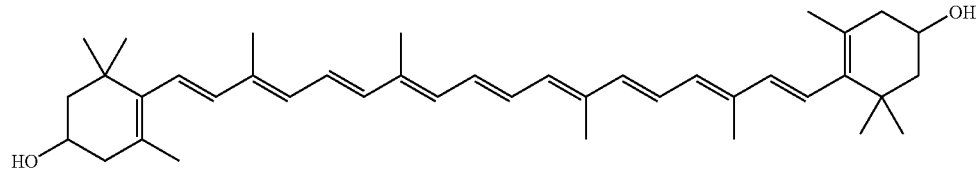

Zeaxanthin

Whereas lutein is the major xanthophyll in marigold flowers, some current varieties yield extract products with zeaxanthin ratios [zeaxanthin/(lutein+zeaxanthin)] typically in the 3 to 5 percent range (See Product Profile, Kemin Foods L.C., 600 E. Court Ave. Suite A, Des Moines, Iowa 50309). As is seen from the results hereinafter, zeaxanthin to lutein ratios obtained using 'Scarletade' are typically about 4 to about 7 percent. Thus, these known xanthophyll marigolds exhibit a zeaxanthin ratio of about 3:100 to about 7:100.

Moehs et al., *Plant Mol. Biol.*, 45:281–293 (2001) analyzed the biosynthesis of carotenoids in ornamental varieties of *T. erecta*, including a so-called wild type that had dark orange flowers, and plants with yellow, pale yellow and white flowers. Among other findings, those workers reported that although the different plants had a range in flower color from white (mutant) to dark orange, the differences in those flower colors were said to be due to the accumulation of very different amounts of the same carotenoid, lutein, rather than to accumulation of different carotenoid products or intermediates. The differences among the plants studied appeared to relate primarily to regulation of flux through the carotenoid pathway, rather than to the specific type of carotenoid produced or the accumulation of biosynthetic intermediates.

In addition, the so-called wild-type and mutant (white-flowered plant) leaves were reported to contain about the same relative quantity of carotenoid pigments, regardless of flower color. Those pigments were different from the pigments present in the petals. Thus, the only pigment reported for petals was lutein, whereas the leaves were reported to contain lutein as well as β-carotene, violaxanthin and neoxanthin. As is seen from FIG. 1, β-carotene but not lutein can be a precursor to the latter two pigments.

The Moehs et al., authors also compared the *T. erecta* genes they isolated with similar carotenoid-producing genes obtained from the leaves of *Arabidopsis thaliana* (Pogson et al., hereinafter). Identities between the gene products of about 70 to about 80 percent were reported at the protein level, with a higher level if putative plastid targeting signal peptides were excluded, and a lower level of identity at the DNA level. In leaves of *A. thaliana*, lutein is the predominant carotenoid, with β-carotene, violaxanthin and neoxanthin also being formed, but no zeaxanthin being normally accumulated.

Carotenoid biosynthesis in *T. erecta* is a complex system involving many genes and possibly two pathways. The impact of genetic mutations on carotenoid production cannot be predicted a priori. However, classic breeding techniques have produced 'Orangeade", 'Deep Orangeade' and 'Scarletade' *T. erecta* variants that produce the elevated levels of xanthophylls noted above. These relatively recently bred available varieties have not been subject to treatments that induce genetic mutations in an attempt to increase the zeaxanthin ratios.

Several workers have examined the effects of mutagens such as gamma irradiation, ethyl methanesulfonate (EMS) and nitrosomethylurea (NMU) on flowering plants, including marigolds. For example, Zaharia et al., *Buletinul Institutului Agronomic Cluj-Napoca. Seria Agricultura* 44(1): 107–114 (1991) reported on the chlorophyll-deficient effects of carotenoids in the coleoptile after seeds of *Zinnia elegans, Tagetes erecta* and *Callistephus chinensis* were irradiated with gamma irradiation in varying amounts. A paper by Geetha et al., *Acta Botanica Indica*, 20(2):312–314 (1992) reports on the chlorophyll deficient effects of gamma irradiation on *Tagetes patula*.

Diaconu, *Agronomie*, 34(1):17–21 (1991) reported on the effects of EMS on germinating seeds from $F_2$ polycrosses of commonly-called pot marigolds, or *Calendula*, that are not even of the genus *Tagetes*. Those workers noted a wide variation in flower color, inflorescence structure, yield and content of biologically-active substances in $M_2$–$M_4$ plants.

A study by Pogson et al., *Plant Cell*, 8:1627–1639 (1996) used EMS to mutagenize plants of *Arabidopsis thaliana*. This detailed study of 4000 $M_2$ lines reported finding two loci in the carotenoid biosynthetic pathway in leaves that are involved with the production of lutein from γ-carotene. Those loci were referred to as lut1 and lut2. The lut2 locus was reported to be associated with the lycopene ε-ring cyclase enzyme, whereas the lut1 locus was reported to be associated with the lycopene ε-ring hydroxylase. Those workers noted (page 1631) that a decrease in lutein production was compensated for by an equimolar change in the abundance of other carotenoids, although only small amounts of those changes were due to an increased production of zeaxanthin.

Cetl et al., *Folia Fac. Sci. Nat. Univ. Purkynianae Brun Biol.*, 21(1):5–56 (1980) reported extensive studies with *T. erecta* and other *Tagetes* species that from the meager descriptions appeared to all be ornamental varieties. Among those studies, those authors examined the effects of various concentrations of NMU on *T. erecta* seeds, and examined more than about 2000 plants. All $M_2$ plants deviating from the phenotype of the parental cross were recorded, and $M_3$ plants from $M_2$ seeds of the phenotypically different plants were studied.

Those workers assayed plant height, plant diameter, flower head diameter and height of the flower head, as well as time to flowering, branching amount, branch length, cotyledon and leaf size, and flower stalk length. No mention is made regarding flower color or carotenoid levels in the leaves or petals.

Published PCT application WO 00/32788 of DellaPenna et al. asserts of a method of regulating carotenoid biosynthesis in marigolds. Those workers provide polynucleotide sequences said to be those that encode the lycopene β-ring cyclase and lycopene β-ring hydroxylase needed for the preparation of zeaxanthin from lycopene. Also disclosed is a lycopene ε-ring cyclase useful along with the lycopene β-ring cyclase for the preparation of α-carotene from lycopene. No teaching of the lycopene ε-ring hydroxylase needed for lutein production is provided.

Carotenoid biosynthesis is said in PCT application WO 00/32788 to be regulated by expression of a carotenoid synthesizing enzyme-encoding gene already present in marigolds such as those noted above, or by use of an anti-sense RNA encoded by such a nucleotide sequence provided. No evidence of such regulation is provided in the application. The phenomenon known as co-suppression by which the addition of a homologous gene causes both the native gene and transgene not to be expressed is not dealt with by those workers. [See for example, Fray et al., *Plant Mol. Biol.*, 22:589–692 (1993) or Finnegan et al., *Bio/Technology*, 12:883–888 (September 1994).]

U.S. Pat. No. 6,383,474 to Soudant et al. teaches that phytoene and phytofluene, together, are effective in preventing damage caused from oxidation and exposure to UV light. This combination is said to be useful as a topical preparation, as a pharmaceutical or as a food additive.

β-Carotene and lycopene are well-known food additives, with lycopene consumption recently being reported to provide a reduced risk of prostate cancer. [See, Giovannucci et al., *J. Natl. Cancer Inst.*, 87(23):1767–1776 (1995).] Lycopene is naturally present as the red pigment in tomato skins, whereas β-carotene is the primary carotenoid pigment in carrots. Hauptmann et al. U.S. Pat. No. 5,618,988 teaches the preparation of carotenoid pigments such as β-carotene in storage organs of transformed plants such as carrots. Ausich et al. U.S. Pat. No. 5,858,700 teaches the isolation of lycopene crystals from an oleoresin as can be prepared from tomato skins. The structural formulas of lycopene and β-carotene are shown below.

that encodes a protein having ketolase enzyme activity from *Adonis aestivalis,* a plant species having deep red flower color due in part to the accumulation of the ketocarotenoid astaxanthin.

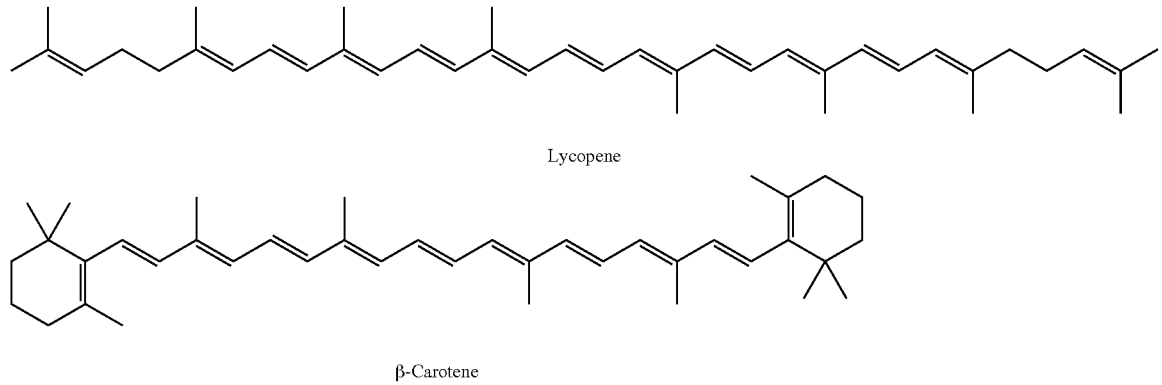

Lycopene

β-Carotene

An increased ratio of zeaxanthin to lutein can provide an attractive substrate for biotechnological production of additional xanthophylls including the red xanthophyll, astaxanthin. Astaxanthin is widely used as a pigmenting agent for cultured fishes and shellfishes. The complete biomedical properties of astaxanthin remain to be elucidated, but initial results suggest that it could play an important role in cancer and tumor prevention, as well as eliciting a positive response from the immune system. [See Tanaka et al., *Carcinogenesis* 15(1):15–19 (1994); Jyonouchi et al., *Nutrition and Cancer* 19(3):269–280 (1993) and Jyonouchi et al., *Nutrition and Cancer* 16(2): 93–105 (1991).]

Astaxanthin supplied from biological sources, such as crustaceans, yeast and green algae is limited by low yield and costly extraction methods when compared with that obtained by organic synthetic methods. Usual synthetic methods however, produce by-products that can be considered unacceptable. It is therefore desirable to find a relatively inexpensive source of (3S,3'S) astaxanthin to be used as a feed supplement in aquaculture and as a valuable chemical for other industrial uses.

One approach to increase the productivity of astaxanthin production in a biological system is to use genetic engineering technology. Genes suitable for this conversion have been reported.

For example, Misawa et al. (See U.S. Pat. No. 6,150,130) specified DNA sequences including one isolated from the marine bacteria *Agrobacterium aurantiacus* sp. nov. MK1 or *Alcaligenes* sp. PC-1 that encodes a gene, referred to as crtW, used in the production of astaxanthin from zeaxanthin as a substrate by way of 4-ketozeaxanthin. Kajiwara et al. (See U.S. Pat. No. 5,910,433) identified a polynucleotide molecule, referred to as bkt, isolated from *Haematococcus pluvialis* that encodes a polypeptide having a beta-C-4-oxygenase activity for the production of (3S,3'S)astaxanthin from a host microorganism or a plant. In addition, Hirschberg et al. (See U.S. Pat. No. 5,965,795) described another DNA gene sequence from *Haematococcus pluvialis,* referred to as crtO, that encodes an enzyme that synthesizes astaxanthin from zeaxanthin by way of 4-ketozeaxanthin. Still further, Cunningham (See WO 99/61652) reported isolation of a DNA It would therefore be useful if a marigold plant could be provided whose flower petals or leaves or both contain a commercially useful amount of xanthophylls and an altered ratio of lutein and zeaxanthin such that the usually reported 4 to about 7 percent zeaxanthin level were raised and the amount of lutein were decreased. It would also be useful if the ratios of other pigments could also be raised, and if such a plant had substantially the same phenotypical characteristics as a usual marigold plant grown adjacent to it. It would be further useful if a marigold could be produced that accumulated β-carotene or lycopene or both in the flower petals or leaves or both. The present invention provides several marigold plants, flower petals, leaves, seed that produces them, hybrids, oleoresins, mixtures of zeaxanthin and lutein, lycopene and β-carotene in proportions not normally found in marigolds, as well as comestible materials containing zeaxanthin, lutein, α-cryptoxanthin, antheraxanthin, neoxanthin and violaxanthin, lycopene, phytoene and β-carotene dissolved or dispersed in a comestible medium.

BRIEF SUMMARY OF THE INVENTION

The present invention contemplates marigold plants whose petals, leaves or both flower petals and leaves contain one or more of an enhanced zeaxanthin ratio, an enhanced neoxanthin plus violaxanthin ratio, an enhanced β-carotene ratio, an enhanced lycopene ratio, an enhanced α-cryptoxanthin ratio, an enhanced phytoene ratio or an enhanced phytofluene ratio compared to such a ratio present in a non-mutant marigold. In addition, the flower petals often contain a measurable amount of zeta-carotene (ζ-carotene), whereas that compound is not measurable; i.e., is present at less than 0.1 or 0.2 percent, in the petals of a non-mutant marigold plant.

A stated ratio is determined as a percentage of the first-named pigment divided by the sum of the percentages of that pigment and lutein as determined after saponification by chromatographic techniques discussed hereinafter. Thus, the zeaxanthin ratio is illustratively defined herein as [zeaxanthin %/(zeaxanthin %+lutein %)].

Preferably the petals, leaves or both the petals and leaves of such a plant at least exhibit a zeaxanthin ratio greater than about 1:10, preferably greater than about 2:10, up to about 1.0. That ratio can be up to one because lutein cannot be detected in some leaves and is present in a very small amount relative to another pigment such as zeaxanthin in petals. In some embodiments, the flower from which the petals are taken has a carotenoid content of about 4 to about 25 mg/g dry weight, whereas in other plants the petal carotenoid content can be lower. The carotenoid content of leaves is typically about 0.5 to about 1.25 mg/g dry weight. The flower petals and leaves are typically present in comminuted form.

Another aspect of the invention contemplates a marigold plant, or a regenerable portion thereof, whose flower petals or leaves or both contain one or more of an enhanced zeaxanthin ratio, an enhanced neoxanthin plus violaxanthin ratio, an enhanced β-carotene ratio, an enhanced lycopene ratio, an enhanced α-cryptoxanthin ratio, an enhanced phytoene ratio or an enhanced phytofluene ratio and preferably at least a zeaxanthin ratio that is greater than about 1:10, preferably greater than about 2:10, and up to about 1.0. The petals of a contemplated plant typically contain a measurable amount of zeta-carotene, as discussed before.

Some contemplated plants have flower petals that contain little if any xanthophylls and rather contain a total of about 50 percent or more β-carotene and lycopene isomers. The flower petals of these plants are orange to red from carotenoid pigments which colors are not normally found in marigolds. Marigolds can exhibit some red coloration due to cell sap-soluble anthocyanin pigments.

The plant that produced the desired petals and leaves is a mutant whose phenotype except as to carotenoids can be substantially the same as that of an adjacently-grown non-mutant plant, or that phenotype can be different. In one aspect, a contemplated marigold plant is an inbred or hybrid between another contemplated mutant plant and a non-mutant in which the non-mutant plant is a hybrid neither of whose parents are mutants. In another aspect, the contemplated marigold plant is a cross (hybrid) of two mutant parents.

A contemplated plant in one embodiment is typically a hybrid one of whose parents resulted from the mutation or later generation hybrid. A contemplated marigold plant of one aspect contains an amount of carotenoids, measured as the saponified pigments extractable from the flowers, that is about 4 to about 25 grams per kilogram of dry flowers or about 4 to about 25 mg/g dry weight. A contemplated marigold of another aspect contains a lesser carotenoid content. The pollen and an ovule of such a plant are separately contemplated. The regenerable portion of such a contemplated plant comprises cells that include embryos, meristems, pollen, leaves, anthers, roots, root tips, and flowers, or protoplasts or callus derived therefrom.

Another embodiment contemplates a seed that on planting in a suitable environment and growth to maturity yields a marigold plant whose flower petals or leaves or both contain one or more of an enhanced zeaxanthin ratio, an enhanced neoxanthin plus violaxanthin ratio, an enhanced β-carotene ratio, an enhanced lycopene ratio, an enhanced α-cryptoxanthin ratio, an enhanced phytoene ratio or an enhanced phytofluene ratio. Preferably, an above-noted ratio is greater than at least about 1:10, more preferably greater than about 2:10, and up to about 1.0. The petals of a contemplated plant again typically contain a measurable amount of zeta-carotene, typically at least 1 percent or more, as discussed before.

A mutant marigold plant oleoresin having one or more of an enhanced zeaxanthin ratio, an enhanced neoxanthin plus violaxanthin ratio, an enhanced β-carotene ratio, an enhanced lycopene ratio, an enhanced α-cryptoxanthin ratio, an enhanced phytoene ratio or an enhanced phytofluene ratio relative to an oleoresin from a non-mutant marigold. Again, a noted ratio is preferably at least greater than about 1:10, more preferably greater than about 2:10, and up to about 1.0. A contemplated oleoresin also usually contains a measurable amount of zeta-carotene, as discussed before.

A food additive comprised of substantially whole or partial marigold petals in dry or native form is also contemplated. Such contemplated petals can be from any of the plants discussed herein, all of which exhibit one or more of an enhanced zeaxanthin ratio, an enhanced neoxanthin plus violaxanthin ratio, an enhanced β-carotene ratio, an enhanced lycopene ratio, an enhanced α-cryptoxanthin ratio, an enhanced phytoene ratio or an enhanced phytofluene ratio relative to a petal from a non-mutant marigold. One group of such petals contains zeaxanthin esters and is substantially free of both neoxanthin and violaxanthin, with zeaxanthin constituting at least about one-half of the extractable carotenoids and being measured as the dialcohol after saponification.

A composition suitable for use as a food or feed supplement containing one or more marigold-derived carotenoid pigments is also contemplated. The food or feed supplement comprises a mixture of zeaxanthin and lutein fatty acid esters dissolved or dispersed in a comestible medium, wherein the zeaxanthin ratio is greater than about 1:10, preferably greater than about 2:10, and up to about 1.0. Another composition suitable for use as a food or feed supplement comprises zeaxanthin and lutein dissolved or dispersed in a comestible medium, wherein the zeaxanthin ratio is greater than about 1:10, preferably greater than about 2:10, and up to about 1.0. A further composition suitable for food use contains phytoene, lycopene or β-carotene dissolved or dispersed in a comestible medium, wherein the phytoene, lycopene or β-carotene ratio is greater than about 1:10, preferably greater than about 2:10, and up to about 1.0.

Yet another aspect of the invention contemplates a marigold plant, or a regenerable portion thereof, whose flower petals contain zeaxanthin esters and are substantially free of both neoxanthin and violaxanthin, wherein zeaxanthin constitutes at least about one-half of the extractable carotenoids and is measured as the dialcohol after saponification. Another embodiment contemplates a seed that on planting in a suitable environment and growth to maturity yields an above-described marigold plant. A marigold oleoresin whose carotenoids include zeaxanthin esters and are substantially free of both neoxanthin and violaxanthin esters is also contemplated. A carotenoid composition suitable for use as a food or feed supplement that contains at least about one-half zeaxanthin and more than ten percent of one or more other carotenoids but is substantially free of both neoxanthin and violaxanthin is further contemplated.

BRIEF DESCRIPTION OF THE DRAWING

In the drawing forming a part of this disclosure.

Figure 1:
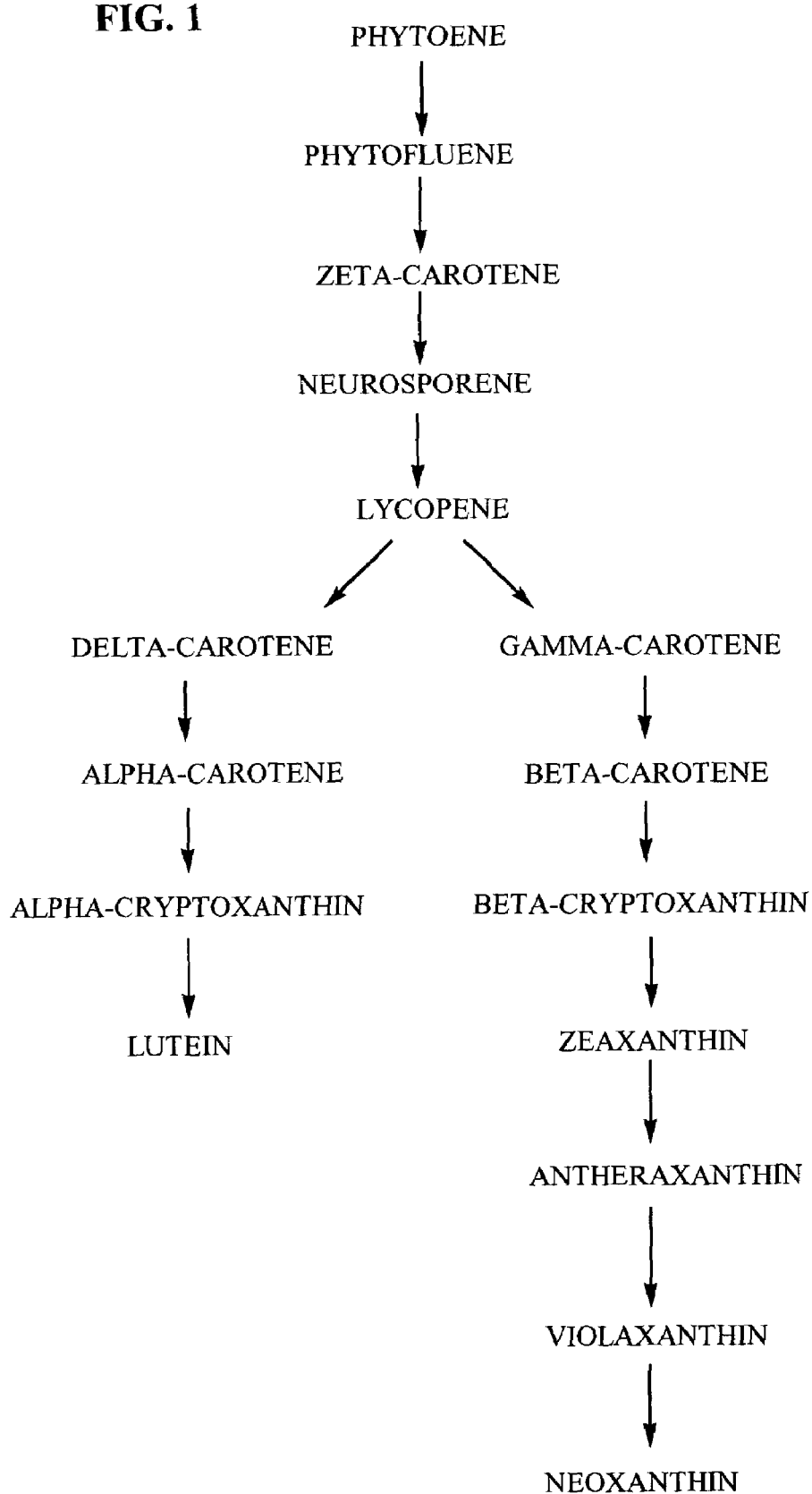
FIG. 1 is a schematic representation of the biological synthesis pathway for the production of lutein and zeaxanthin in plants in which phytoene, the first $C_{40}$ carotenoid in the pathway, is converted in several steps (four arrows) through zeta-carotene (ζ-carotene) to lycopene, after which the pathway splits to form δ-carotene that contains one ε-ring, then α-carotene that contains one ε-ring and one β-ring or to form γ-carotene that contains one β-ring, then β-carotene that contains two β-rings, and after several steps, to lutein or zeaxanthin, respectively, and the zeaxanthin branch continuing to the epoxide-containing xanthophylls antheraxanthin, violaxanthin and neoxanthin.

As used herein, the term "zeaxanthin ratio" is defined as the quantity of zeaxanthin present in a dried flower petal or leaf divided by the quantity of zeaxanthin plus lutein [zeaxanthin/

(lutein+zeaxanthin)] present in that petal or leaf. The "neoxanthin plus violaxanthin ratio" is similarly calculated as the ratio of neoxanthin+violaxanthin divided by the sum of those two pigments plus lutein. The "β-carotene ratio", the "lycopene ratio", the "α-cryptoxanthin ratio", the "phytoene ratio" and the "phytofluene ratio" are similarly calculated using the named pigment amount as the sum of its isomers as the numerator and the sum of that pigment plus lutein as the denominator. Those sums can also be as percentages. The pigment quantities are determined by high performance liquid chromatography (HPLC) after saponification of a dried flower petal or leaf extract as discussed hereinafter so that the amount of each of lutein and zeaxanthin (or other pigment) is measured in the free compound form, e.g., alcohol form for lutein and zeaxanthin, present after saponification rather than in the esterified form that is present in the fresh flower petal, and chlorophyll that may be present in a leaf extract is destroyed. Some of the flower petals and leaves of plants discussed herein contain very low or unmeasurable amounts of lutein or lutein esters, e.g., less than about 0.1–0.2 percent. When that is the case, the amount of lutein in the denominator of a ratio approaches zero and the ratio approaches one.

The word "oleoresin" is used herein to mean an extract of plant tissues that contains plant pigments such as the xanthophylls discussed herein in their esterified forms, sometimes accompanied by amounts of other plant products and pigments such as other carotenoids such as β-carotene, as well as small amounts of solvent such as hexane or acetone, typically less than 1 percent organic solvent. Xanthophylls are typically present as mono- or diesters in flower petals and are typically present as free alcohols in marigold leaves. Carotenes such as β-carotene or lycopene are present as free, non-chemically-combined compounds. Chlorophyll is present in marigold leaves and largely absent in the petals. Thus, an oleoresin prepared from flower petals contains xanthophyll esters and/or hydrocarbon carotenes and is largely free of chlorophyll, whereas an oleoresin prepared from marigold leaves contains chlorophyll and free xanthophylls and carotenes. Both chlorophyll and xanthophyll esters are decomposed by saponification of the oleoresin. A contemplated oleoresin is a solid or semi-solid material.

DETAILED DESCRIPTION OF THE INVENTION

The present invention contemplates marigold plants, seeds, flower petals, leaves and materials that can be prepared therefrom. A contemplated plant additionally has flower petals, leaves or both that contain an enhanced ratio of one or more carotenoids as compared to previously known marigold plants. The petals and/or leaves of a contemplated plant thus contain one or more of an enhanced zeaxanthin ratio, an enhanced neoxanthin plus violaxanthin ratio, an enhanced β-carotene ratio, an enhanced lycopene ratio, an enhanced α-cryptoxanthin ratio, an enhanced phytoene ratio or an enhanced phytofluene ratio. The leaves or petals of a contemplated plant can be free of lutein; i.e., the leaves or petals contain lutein at less than about 0.1 to about 0.2 percent of the extractable, saponified carotenoids. These contemplated marigold plants are T. erecta, as compared to T. patula or T. tenuifolia, or other Tagetes species. In addition, a contemplated plant can be a xanthophyll marigold, as such plants have been described before and are understood by workers of skill in this art.

The usual ratio of zeaxanthin to zeaxanthin+lutein in marigold petals is on the order of about 1:15 to about 1:25, so that when only zeaxanthin and lutein amounts are used for calculations, zeaxanthin is about 5 to about 7 percent of the amount of lutein plus zeaxanthin. An article by Quackenbush et al., J. Assoc. Off. Agri. Chem., 55:617–621 (1972) reported a zeaxanthin to lutein ratio in one group of American yellow T. erecta marigold flower petals that was unusually high at about 1:4.4, whereas the total concentration of xanthophylls in those petals was unusually low at about 0.4 mg/g dry weight. A Mexican variety was said by those authors to contain 11.1 percent zeaxanthin when lyophilized petals were assayed and 3.8 percent when fresh petals were assayed. The higher value is not in keeping with the remainder of the data and is believed to be incorrect. The preferred zeaxanthin ratio in petals contemplated here is even larger, being greater than about 1:10 and preferably greater than about 2:10, on up to about 1.0, as will be discussed hereinbelow, and the amount of petal carotenoids is preferably at least about 4 mg/g dry weight.

A contemplated marigold plant has flower petals that contain a zeaxanthin ratio greater than about 1:10 and preferably greater than about 2:10. More preferably still, a contemplated marigold plant has flower petals that contain a zeaxanthin ratio greater than about 3:10. Most preferably, that ratio is greater than 5:10, and can be about 1.0. The flower from which the petals are taken has a carotenoid content of about 4 to about 25 mg/g dry weight, and preferably about 10 to about 20 mg/g dry weight. Such a marigold plant also preferably has leaves that contain a zeaxanthin ratio greater than about 1:10 and preferably greater than about 2:10. More preferably still, a contemplated marigold plant has leaves that contain a zeaxanthin ratio greater than about 3:10. Most preferably, that ratio is greater than 5:10, and can be about 1.0. The contemplated leaves have a carotenoid content of about 0.2 to about 1.25 mg/g dry weight, and preferably about 0.5 to about 1 mg/g dry weight.

In some embodiments, the lutein concentration of the petals of a contemplated plant is about 80 to about 90 percent of the lutein present in a parental, non-mutant plant. In other embodiments, the amount of lutein is less than about 75 percent of that present in a non-mutant plant. In still further embodiments, the amount of lutein present in the flower petals is less than about 15 percent of that present in the petals of a non-mutant marigold plant. Indeed, lutein can be substantially absent from the leaves or petals of particularly preferred plants; i.e., present at less than about 0.2 percent of the carotenoids.

A contemplated marigold can also exhibit differences in ratios of one or more other pigments relative to lutein. Thus, the neoxanthin plus violaxanthin ratio in a parental plant can be about 0.01 to about 0.02 for a non-mutant petal extract and about 0.17 to about 0.33 in leaves. That ratio in contemplated mutant plant petals and leaves of one preferred embodiment is about 1:5 (0.2) to about 1:1 (one). In some Tables hereinafter, neoxanthin and violaxanthin are measured together as they were difficult to separate chromatographically.

The β-carotene ratio in non-mutant plants is typically about less than 0.007 for flower petals and about 0.25 to about 0.3 for leaves. In a contemplated mutant marigold, that ratio is about 1:10 and preferably greater than about 2:10 in petals. More preferably still, a contemplated marigold plant has flower petals that contain a β-carotene ratio greater than about 3:10. Most preferably, that ratio is greater than 5:10, and can be about 1.0. The ratio for mutant marigold leaves is about 0.4 to one.

Lycopene is normally not found in either marigold leaves or flower petals. The lycopene isomer ratio is typically, therefore zero for a usual, non-mutagenized marigold. A contemplated mutant plant can exhibit a lycopene ratio of about 1:10 and preferably greater than about 2:10 in petals. More preferably still, a contemplated marigold plant has flower petals that contain a lycopene ratio greater than about 3:10. Most preferably and more usually because of the usual absence of lycopene from marigold flower petals, that ratio is greater than 5:10, and is about 1.0.

α-Cryptoxanthin typically constitutes less than one percent of colored carotenoids of non-mutant plant petals and the α-cryptoxanthin ratio is consequently about 0.01 in non-mutant flower petals. The α-cryptoxanthin ratio is about 0.25 to about 0.9, and is most preferably and usually about one in the petals of preferred mutated plants.

Phytoene can be present in petals at about 3 to about 0.3 percent of the carotenoids in non-mutant plants and can be present at about 35 percent in some mutant flower petals that typically contain a reduced amount of lutein. Exemplary phytoene ratios can be from about 0.3 to about 1 in a contemplated plant as compared to phytoene ratios of about 0.003 to about 0.03 in non-mutant plants. Phytoene concentrations are largely unchanged in leaves of mutant plants as compared to non-mutant plant leaves.

Phytofluene amounts in non-mutant plant petals are typically about the same as those observed for phytoene, whereas the amount present in the petals of a contemplated mutant plant is generally about 40 to about 70 percent of the phytoene amount. The phytofluene ratio for a non-mutant plant is usually about 0.005 to about 0.03, whereas that ratio for a contemplated mutant plant is about 0.2 to about 1. Phytofluene has not been observed in leaf extracts.

The enhancements observed in the above ratios are typically at least about two-fold. In particular embodiments, a ratio can be enhanced by about ten- to about one hundred-fold. Regardless of the percentage of enhancement, the ratio of each of the above carotenoids to each carotenoid plus lutein is 1:10 or greater, and preferably about 2:10 or greater.

The petals or leaves or both of a particular plant can have one or more of the above-recited enhanced ratios. In usual practice, two or more of the before-described enhanced ratios are present. Thus, for example, the zeaxanthin ratio and the β-carotene ratio can be enhanced, the lycopene ratio and the β-carotene ratio can be enhanced, or the zeaxanthin ratio and the neoxanthin plus violaxanthin ratio can be enhanced. Similarly, three or more of the ratios can be elevated.

α-Cryptoxanthin is a particularly interesting compound in that it has been found to be present in relatively high levels in a number of mutants and is not otherwise readily available. Thus, α-cryptoxanthin was present at about 20 to about 40 percent of colored carotenoids in some mutants. The α-cryptoxanthin ratio of such plants was consequently greatly enhanced as compared to those plants whose petals contained more usual carotenoid profile.

The petals of a contemplated plant typically contain a measurable amount of zeta-carotene (ζ-carotene), whereas that pigment is not present in a measurable amount; i.e., present at less than 0.2 percent, in the petals of a non-mutant marigold plant. Typically, zeta-carotene is present in an amount of at least about 1 percent of the petal carotenoids. That amount of zeta-carotene can be in the range of about 3 to about 7 percent in some embodiments, and at about 20 percent in other embodiments.

Measurable amounts of a pigment depend upon the pigment, the separation system used, the chromatographic column used, eluting solvent, as well as a number of other variables well known to skilled workers. For purposes of this disclosure, a pigment is considered absent if its presence is at less than about 0.1–0.2 percent.

Another aspect of the present invention contemplates a marigold plant whose leaves and/or flower petals are substantially free of lutein (i.e., contain lutein at less than about 5 percent by weight of the total weight of carotenoids present), and at least about one-half of whose carotenoids are comprised of zeaxanthin and β-carotene. Thus, together, zeaxanthin plus β-carotene together constitute at least about one-half of the total carotenoids. More preferably, zeaxanthin and β-carotene together constitute about 60 to about 95 weight percent of the carotenoid pigments present in leaves and/or petals of a contemplated plant.

Marigold petals can be used for extraction of their carotenoids and carotenoid esters as well as by themselves as food additives. A contemplated food additive is comprised of whole or partial marigold petals in dry or native (hydrated form as plucked from a flower head) form. The petals so used can be sprinkled on foods such as salads and desserts as a decorative garnish as well as for the benefits obtained from ingesting the carotenoids. Substantially whole petals; i.e., in the form in which the petals are plucked from the flower head, in native form, are preferred for decorative purposes, whereas partial petals such as finely comminuted, dried petals are typically used for additions to cooked foods or for additives to animal feeds.

Such contemplated petals can be from any of the plants discussed herein, all of which exhibit one or more of an enhanced zeaxanthin ratio, an enhanced neoxanthin plus violaxanthin ratio, an enhanced β-carotene ratio, an enhanced lycopene ratio, an enhanced α-cryptoxanthin ratio, an enhanced phytoene ratio or an enhanced phytofluene ratio relative to a petal from a non-mutant marigold. One group of such petals contains zeaxanthin esters and is substantially free of both neoxanthin and violaxanthin, with zeaxanthin constituting at least about one-half of the extractable carotenoids and being measured as the dialcohol after saponification.

Another preferred use of marigold petals is as a food additive comprised of dried, finely comminuted marigold petals. This marigold food product can be referred to as a marigold meal, and can be sprinkled or shaken on or into a food product much as are red pepper flakes or ground oregano leaves.

Such a marigold meal can be prepared from known marigolds such that the petals contain lutein and zeaxanthin as the principal xanthophylls as measured as the dialcohols after saponification, and wherein the zeaxanthin ratio is about 3 to about 7:100. More preferably, the petals contain one or more of an enhanced zeaxanthin ratio, an enhanced neoxanthin plus violaxanthin ratio, an enhanced β-carotene ratio, an enhanced lycopene ratio, an enhanced α-cryptoxanthin ratio, an enhanced phytoene ratio or an enhanced phytofluene ratio. Each of those enhanced ratios is about 1:10 or more, and preferably about 2:10 or greater, as discussed before.

In some embodiments, the petals contain zeaxanthin esters and are substantially free of both neoxanthin and violaxanthin, with zeaxanthin constituting at least about one-half of the extractable carotenoids when measured as the dialcohol after saponification. In other embodiments, petals contain an enhanced lycopene ratio relative to dried, comminuted petals from a non-mutant marigold. In still other embodiments, α-cryptoxanthin is the most abundant carotenoid present in the dried, comminuted flower petals.

In some these embodiments, the lutein present in leaves and/or petals is less than about 3 weight percent and more preferably less than about one weight percent of the extractable carotenoids. The β-carotene present in these petals and/or leaves can be present at about 5 to about 80 percent of the carotenoids.

A further aspect of the invention contemplates a marigold plant, or a regenerable portion thereof, whose flower petals contain zeaxanthin and are substantially free of both neoxanthin and violaxanthin, wherein zeaxanthin constitutes at least about one-half of the extractable carotenoids and is measured as the dialcohol after saponification. Thus, the zeaxanthin present is typically present as a mono- or diester as noted elsewhere, but is measured as the free diol after saponification of a petal extract. Surprisingly, a plant contemplated here has flower petals that are substantially free of both neoxanthin and violaxanthin.

As is seen from the data in Tables 6a–6c, exemplary petals of prior art plants and several mutant plants prepared herein have enhanced rations of zeaxanthin to zeaxanthin plus lutein and readily measurable amounts of neoxanthin and violaxanthin. On the other hand, the data for the plants of Tables 8a–8c illustrate several plants wherein zeaxanthin constitutes one-half or more of the extractable carotenoids and neoxanthin and violaxanthin amounts are less than a measurable amount using the procedures discussed hereinafter, so that the flowers of such plants are substantially free of those two carotenoids.

Another embodiment contemplates a seed that on planting in a suitable environment and growth to maturity yields a marigold plant as described immediately above.

A marigold oleoresin whose carotenoids include zeaxanthin esters and are substantially free of both neoxanthin and violaxanthin esters is also contemplated. A carotenoid composition suitable for use as a food or feed supplement that contains at least about one-half zeaxanthin and more than ten percent of one or more other carotenoids but is substantially free of both neoxanthin and violaxanthin is further contemplated.

As already noted, xanthophylls such as lutein and zeaxanthin are present in flower petals primarily as mono- or diesters of fatty acids such as lauric, myristic, palmitic, stearic, oleic or the like, rather than as free diol compounds. As such, when a zeaxanthin or other xanthophyll ratio is discussed herein, that ratio is determined by extracting one or more flower petals with hexane or other appropriate solvent to obtain a composition such as an oleoresin comprised of esterified xanthophylls. That composition is then saponified using a base such as potassium hydroxide to cleave the esters and form free carotenoid dialcohols. The free carotenoid xanthophyll alcohols are thereafter separated from the saponification reaction mixture and separated as desired using high performance liquid chromatography (HPLC). The ratios of materials present are determined by the areas under the appropriate HPLC peaks using standard methods of integration.

It is to be noted that Table 10, hereinafter, illustrates that some contemplated plants exhibit free xanthophylls in their petals rather than the usually found xanthophyll esters. As such, free xanthophyll-containing edible foods and feed supplements can be prepared that do not require saponification.

The analytical method utilized herein to determine the pigment ratios is exemplified hereinafter, and provides similar results to those published by others, with different specific techniques being used by different laboratories largely for reasons of convenience. Using the procedure preferred here, flowers approximately 98 percent fully opened are selected for analysis. Petals are removed about one-third of the distance from the flower center from the selected flowers.

Leaves can be harvested and extracted at substantially any time. Xanthophylls are typically present as free compounds in leaves as are carotenes. Chlorophyll present in leaves is also extracted with the carotenoid pigments so assays are carried out after saponification of the extract as that treatment destroys chlorophyll. Leaves are assayed for carotenoid content as are the petals.

A standard analytical method used in the industry for determining carotenoid levels in plant extracts is that of the AOAC 1984, *Official Methods of Analysis* (14$^{th}$ ed), the Association of Official Analytical Chemists, Arlington, Va., USA, the results of whose assays are similar to those obtained herein.

A contemplated marigold plant is a mutant of a parental line. That is, a first line or cross or seed is treated with a mutagen (mutagenized) to provide a mutagenized plant that is typically self-pollinated (selfed) one or more times. A plant contemplated herein can arise from the mutagenesis itself, from one of the selfings or from a cross of a mutagenized plant or offspring with another mutagenized or non-mutagenized plant.

Substantially any kind of mutagen can be used to produce a contemplated plant, and exemplary mutagens are discussed hereinafter. Although some contemplated mutant marigolds have a phenotype that is substantially different from that of adjacently-grown non-mutant marigold parental plant, other contemplated mutants exhibit substantially the same phenotype as that of an adjacently-grown non-mutant parental plant, except for phenotypic traits related to carotenoids. More specifically for the latter plants, when one compares plant properties such as plant height, plant diameter, flower head diameter, flower head height, time to flowering, branching amount, length of branches, flower stalk length, hypocotyl length, cotyledon length and cotyledon width between a parent and a mutant plant, the values of those properties for some contemplated mutant plants are each within about 90 percent of those of the parental plant, including the standard deviations in the measurements. More preferably, the values for those properties of the mutant are within about 95 percent of the parent, and most preferably, the values are the same, within the standard deviation. On the other hand, other mutant plants differ greatly in one or more phenotypic traits.

A carotenoid-related phenotypic difference between the parental and mutant plants is the quantity of xanthophyll or carotene pigment that can be obtained from the flowers of the mutant. Parental plants such as 'Scarletade' or 'Deep Orangeade' typically have about 10 to about 18 mg/g dry whole flower head weight of extractable xanthophyll pigments and contain very little carotenes. A contemplated mutant plant having a high zeaxanthin ratio preferably contains about the same amount of carotenoid in the flower petals, but can contain as little as about 4 mg/g dry weight, particularly where the ratio of zeaxanthin to lutein is very high such as about 9:1 or greater. Other mutants can contain little xanthophylls and a relatively large amount of one or more carotenes.

The leaves of a contemplated marigold can also exhibit a phenotypic difference between the parental and mutant plants in one or more of several respects, including the carotenoid content as well as one or more of the before-discussed carotenoid ratios present in the leaves as measured in a saponified oleoresin. The previously noted paper of Moehs et al., *Plant Mol. Biol.*, 45:281–293 (2001) reported that leaf carotenoid ratios and contents were constant, whereas carotenoid concentration in the petals differed. Here, it is found that one or more of the before-mentioned zeaxanthin ratio, antheraxanthin ratio, neoxanthin plus violaxanthin ratio, phytoene ratio, phytofluene ratio, β-carotene ratio, lycopene ratio and α-cryptoxanthin ratio in mutant plants differed considerably from parental non-mutant plants. In addition, the petals of the mutant plants examined typically exhibited a measurable amount of zeta-carotene, whereas no measurable amount zeta-carotene was observed to be present in the parental non-mutant plants.

Phenotypic comparisons are made between adjacently-grown plants. As used herein, the term "adjacently-grown" is used to mean plants grown under as similar conditions of light, heat, growth medium, humidity and nutrients as can be achieved so that growth conditions do not govern the phenotype. For greenhouse-grown plants, "adjacently-grown" means plants grown under conditions as similar as possible on the same bench. For field-grown plants, "adjacently-grown" means plants grown under conditions as similar as possible in the same or adjoining fields.

Mutagenic agents useful for altering plants are well known in the art, as are methods of using such agents. Exemplary chemical mutagens include nitrosomethylurea (NMU), ethyl methanesulfonate (EMS), methyl methanesulfonate, diethyl sulfate, nitrosoguanidine, and ethylnitrosourea of which EMS is preferred herein. NMU can be used as discussed in Cetl et al., *Folia Fac. Sci. Nat. Univ. Purkynianae Brun. Biol.*, 21(1): 5–56 (1980), whereas EMS is typically utilized at about 0.25 to about 1 percent by volume (v/v), and preferably at about 0.2 to about 0.8 percent. Gamma irradiation is also a useful mutagenic agent when used to irradiate seeds at a dose of 200 to about 20,000 rads (0.2 to about 20 krads).

In addition to chemical mutants, plants can also be mutated using ionizing radiation as by gamma rays or neutrons and also by recombinant DNA techniques. As is illustrated hereinafter, ionizing radiation and recombinant DNA techniques such as gene silencing can also be used to effect alterations in carotenoid profiles. These plants can be thus referred to as chemically-induced, ionizing radiation-induced and recombinantly-induced mutants, respectively. As a consequence, a mutant marigold is defined herein as a marigold plant obtained by chemically-induced mutation, ionizing radiation-induced mutation or recombinantly-induced mutation.

Thus, gamma rays and fast neutron bombardment have been used for other plants to cause deletions of one or more genes. Gene silencing can be effected by over expression of a sense strand of a gene that leads to down-regulation via a mechanism referred to as co-suppression. Down regulation can also be achieved by expression of antisense genes for one or more enzymes present in a carotenoid-production pathway. Still further techniques are well known to workers skilled in this art.

Regardless of the mutagen used, the phenotype of the resulting mutant plant, including carotenoid-related traits such as the zeaxanthin ratio and the amount of xanthophylls in the petals, is usually substantially identical to that of the parent, so that a very large percentage of the mutants obtained are not useful. In addition, plants seeming to have the same phenotype as the parent need to be screened to locate a desired mutant plant. Those screenings, although tedious, are routinely carried out and involve analysis of carotenoid pigments from one or more single flower petals or leaves or both. Thus, the preparation of a desired mutant is a relatively rare, but repeatable event. For example, in one study herein, twenty-three useful mutants were obtained from almost 22,000 mutant plants examined. In another study, about twenty-four useful mutants out of about 8,200 examined plants were obtained.

As already noted, a contemplated plant can be a plant that grows from the mutagenized seed or can be a selfing or cross. In one preferred embodiment, a contemplated marigold is a hybrid formed by crossing the flowers of two plants that arose from two different mutagenized plants from independent $M_1$ plants ($M_2 \times M_2$). In another embodiment, a contemplated marigold is a hybrid formed by crossing the flowers of one plant that arose from one mutagenized plant with a non-mutagenized plant. In still another embodiment, a contemplated plant is a hybrid formed by back-crossing a hybrid with one or the other of its immediate parental flowers. The product of the crossing of two different hybrid plants is contemplated as is the product of the selfing of a hybrid.

As has already been mentioned, a contemplated marigold plant can itself be an immediate product of a mutation event, such as a product of the seed produced after the mutation process. That plant can also be a product of one or more crosses of one mutant with another or of mutant selfings. A contemplated plant can also be the result of a cross between mutant and non-mutant parental plants. The produced plants are screened and selected for desired carotenoid characteristics.

The present invention also contemplates the pollen and an ovule of a contemplated plant. The regenerable portion of a contemplated plant is also itself contemplated and includes cells selected from the group consisting of embryos, meristems, pollen, leaves, anthers, roots, root tips, and flowers, or protoplasts or callus derived therefrom. Methods for regenerating plants from cells are well known to those skilled in the art, and dicotyledonous plants such as marigolds are particularly amenable to such regeneration.

A marigold oleoresin comprised of fatty acid esters of lutein and zeaxanthin in which the zeaxanthin ratio is greater than about 1:10 and preferably greater than about 2:10 is also contemplated. More preferably, that ratio is greater than about 3:10 and is most preferably about 1.0. A contemplated marigold oleoresin contains a zeaxanthin ratio as is present in the petals or leaves of a contemplated marigold as discussed before. Oleoresins are items of commerce and are sold to processors for further treatment in the production of human or other animal food or feed supplements. A contemplated oleoresin also typically contains a measurable amount of zeta-carotene.

In an illustrative marigold oleoresin preparation, xanthophyll esters; i.e., zeaxanthin or mixture of zeaxanthin and lutein esters and possibly other xanthophyll esters and carotenes such as zeta-carotene, are extracted from dried marigold flowers with hexane, acetone, ethyl acetate, toluene, tetrahydrofuran (THF) and the like organic solvent, or a mixture thereof. The extraction is carried out according to procedures known in the art. The solvent(s) is removed, resulting in an extract that typically contains a high level of the xanthophyll esters and is about 99 percent and preferably about 99.9 percent free of the extracting organic solvent; i.e., contains less than about 1 percent and preferably less than about 0.1 percent organic solvent by weight. The resulting solvent-free extract is referred to as a marigold oleoresin. A leaf extract is similarly prepared, and contains free xanthophylls, carotenes and chlorophyll.

A composition suitable for use as a food or feed supplement for human or other animals such as poultry like chickens and turkeys, fish like trout and salmon and crustaceans like shrimp, lobsters and crabs is also contemplated. A contemplated food or feed supplement can be used to provide color to the skin and fat of those animals as well as to the egg yolks of such animals, and particularly chickens.

One food or feed supplement comprises a mixture of fatty acid esters of zeaxanthin alone or zeaxanthin, lutein and other carotenoids as are present in a marigold oleoresin. That mixture of marigold-derived mostly fatty acid esters is dissolved or dispersed in a comestible medium, wherein the zeaxanthin and lutein fatty acid esters are present at a zeaxanthin ratio that is greater than about 1:10, preferably greater than about 2:10, more preferably greater than about 3:10, and up to about 1.0. This food or feed supplement can thus be prepared by suitable purification of a before-described oleoresin as by dissolution and filtration, followed by dissolution or dispersion of the purified mixed esters in an appropriate comestible medium.

An oleoresin and food product can be similarly prepared from marigold petals, leaves or both using plants that exhibit enhanced levels of the other pigments noted herein such as phytoene, β-carotene and lycopene, for example. Where the desired marigold-derived pigment(s) is a carotene, rather than a xanthophyll, saponification is typically not needed to hydrolyze an ester as no esters are present. However, as noted in U.S. Pat. No. 5,858,700, a saponification reaction can be used to free a pigment such as lycopene from the surrounding plant materials.

In some embodiments, the comestible medium is an edible triglyceride oil, whereas in other embodiments the comestible medium is a binding agent such as is frequently found in pharmaceutical products such as pills and tablets (a pharmaceutically acceptable binding agent). For tablets or capsules, the carotenoid content such as the xanthophyll ester content of the admixture is typically about 0.1 to about 25 milligrams per tablet or capsule of carotenoid as can illustratively be measured as free xanthophyll, and more usually about 5 to about 20 milligrams per tablet or capsule.

Binding agents and adhesives preferably impart sufficient cohesion to solids to permit normal processing such as sizing, lubrication, compression and packaging, but still permit a tablet or capsule to disintegrate and the composition to dissolve upon ingestion. Exemplary binding agents include lactose monohydrate, acacia, tragacanth, sucrose, gelatin, glucose, cellulose or saccharide materials such as, but not limited to, microcrystalline cellulose, croscarmellose sodium, hydroxypropyl methylcellulose (HPMC), hydroxypropyl cellulose (Klucel™), ethyl cellulose (Ethocel™), methyl cellulose and sodium carboxymethyl cellulose (e.g., Tylose™), pregelatinized starch (such as National™ 1511 and Starch 1500), polysaccharide acids, alginic acid and salts of alginic acid, magnesium aluminum silicate, polyethylene glycol, guar gum, bentonites, polyvinylpyrrolidone (povidone), and polymethacrylates.

Exemplary edible oils include candelilia, coconut, cod liver, cotton seed, menhaden, olive, palm, corn, soybean, peanut, poppy seed, safflower and sunflower oil. The use of an oil having a relatively high concentration of unsaturated fatty acids is preferred; i.e., the use of an oil having an iodine value of about 100–150 is preferred. The admixture is typically carried out using a high shear mixing apparatus, as is well known. Co-solvents and additives such as ethanol and α-tocopherol, respectively, can also be present as is noted in U.S. Pat. No. 5,382,714.

In another embodiment, the mixture of zeaxanthin and lutein, zeaxanthin alone, or other marigold-derived carotenoid compound such as β-carotene or lycopene, or a mixture is provided in the form of generally spherical small pellets containing 0.5 to about 20 percent, and preferably about 1 to about 4 percent, of the carotenoid that are conventionally referred to as "beadlets". These beadlets can be used admixed in a desired amount into human food such as ready to eat cereals as is disclosed in U.S. Pat. No. 5,270,063 or admixed into chicken or other animal feed as are the beadlets or other particles disclosed for the feed additive in U.S. Pat. No. 5,849,345, U.S. Pat. No. 5,695,794, U.S. Pat. No. 5,605,699 and U.S. Pat. No. 5,043,170.

Exemplary beadlets are water-insoluble and are prepared by encapsulation of a xanthophyll composition by cross-linked gelatin or an alginate such as sodium alginate as is disclosed in U.S. Pat. No. 4,670,247. A water insoluble beadlet containing the desired carotenoid(s) is prepared by forming an emulsion containing the carotenoid(s), water, gelatin, and a sugar. The emulsion is converted into droplets that are individually collected in a mass of starchy powder in such a manner that the particles from the droplets are kept separated from each other until their particulate form is permanently established. The carotenoid-containing particles are separated from the starchy collecting powder, and heat-treated at a temperature of about 90° C. to about 180° C. The heat treatment step insolubilizes the gelatin matrix of the beadlet by a reaction between the carbonyl group of the sugar with the free amino moieties of the gelatin molecule. The resulting beadlets are water-insoluble and exhibit increased stability to the stresses of feed pelleting. The cross-linking process utilizes the ingredients employed in making the beadlet and does not require addition of a cross-linking reagent or additive to the composition.

U.S. Pat. No. 5,695,794 discloses another form of beadlets that can be adapted for use herein as an additive for poultry feed. Thus, beadlets having diameters of about 30 to about 55 microns are prepared by spraying a molten solution of a desired amount of carotenoid(s); i.e., zeaxanthin, a mixture of zeaxanthin and lutein, or other carotenoid mixture described herein, in hydrogenated vegetable oil such as hydrogenated cotton seed oil, wheat-germ oil, safflower oil, soybean oil and the like, that also can contain mono- and diglycerides such as those prepared from hydrogenated soybean mono- and diglycerides, cottonseed mono- and diglycerides and the like, as well as citric acid and 2,6-di-tert-butyl-4-methylphenol (BHT) as antioxidants. Other antioxidants such as ethoxiquin, vitamin E and the like can also be used, as is well known. The molten mixture is sprayed at a temperature of about 160° F. (about 70° C.) into a cyclonic airstream of a spray chiller such as available from Niro, Inc., Columbia, Md. to produce the beadlets that solidify on cooling. The cooled beadlets are dusted with an anticaking agent such as fumed silica, calcium phosphate, powdered starch or cellulose as are well known to form the beadlets that are preferably added to the feed as supplement. An exemplary beadlet contains about 10 to about 100 milligrams of zeaxanthin per gram (mg/g) and preferably at about 10 to about 50 mg/g.

Animal feeds to which a contemplated marigold-derived carotenoid pigment such as zeaxanthin or a zeaxanthin-lutein, β-carotene, lycopene, or a mixture of such pigments are added are well known in the art. The above-noted U.S. Pat. No. 5,849,345, U.S. Pat. No. 5,695,794, U.S. Pat. No. 5,605,699 and U.S. Pat. No. 5,043,170 provide exemplary diets that are particularly useful for poultry. U.S. Pat. No. 5,935,624 and U.S. Pat. No. 2,918,370 provide further illustrative poultry diets.

U.S. Pat. No. 5,258,189 teaches the addition of β-carotene to a ready to eat cereal product for humans in whom the β-carotene is admixed with a cooked cereal product dispersed in a vegetable oil or in dry form. Zeaxanthin or a mixture of zeaxanthin and lutein as discussed elsewhere herein can be used at a desired level in place of β-carotene in a similar food product.

Another composition suitable for use as a food or feed supplement comprises a mixture of a marigold-derived carotenoid pigment such as zeaxanthin and lutein, lycopene, phytoene, β-carotene or the like dissolved or dispersed in a comestible medium, wherein the zeaxanthin ratio present is at a greater than about 1:10, preferably greater than about 2:10, and up to about 1.0. This composition contains saponified xanthophylls that are free zeaxanthin and lutein as compared to the esters that are present in a marigold oleoresin.

The phrase "marigold-derived" is used herein for a carotenoid pigment that is obtained from a mutant marigold as described herein. Thus, substantially all (more than 90, and preferably more than 95 percent) of the carotenoid pigment present in a food or feed supplement of marigold-derived carotenoid pigment is from a marigold, as compared to being from another plant or produced synthetically. The pigment can be a free carotene or xanthophyll (as shown in Table 10, hereinafter) or can be a saponified xanthophyll.

Methods are well known for saponifiying marigold oleoresins to provide free xanthophylls. See, for example, Tyczkowski et al., *Poultry Sci.* 70(3): 651–654, 1991; and U.S. Pat. No. 5,382,714, that lutein was crystallized from the saponified marigold oleoresin by the addition of organic solvents.

In addition, Ausich et al. U.S. Pat. No. 5,648,564 teaches the production of crystalline lutein from a marigold oleoresin by admixing the oleoresin with a composition containing propylene glycol and an aqueous alkali, preferably potassium hydroxide, to form a reaction mixture of which oleoresin and propylene glycol together constitute at least 75 weight percent. The reaction mixture so formed is maintained at a temperature of about 65° C. to about 80° C. for a time period (typically at least 3 hours) sufficient to saponify the xanthophyll ester and form a saponified reaction mixture that contains free xanthophyll in the form of crystals. The saponified extract is admixed with a diluting amount of water to dissolve the water-soluble impurities and reduce the viscosity of the reaction mixture. The diluted admixture is gently admixed until homogeneous and then filtered to collect the xanthophyll crystals. The collected xanthophyll crystals are washed with warm water, and dried. No organic solvent other than propylene glycol is used in the isolation and purification of the xanthophyll from the xanthophyll ester-containing oleoresin. The dried xanthophyll crystals so formed are typically admixed with a comestible medium such as the triglyceride discussed above. The xanthophyll content of the admixture is typically about 0.1 to about 35 percent by weight, and preferably about one to about ten percent by weight.

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

EXAMPLE 1

EMS Treatment of *Tagetes erecta* 'Scarletade'

Seeds of *Tagetes erecta* xanthophyll marigold denominated 'Scarletade' (commercially available from PanAmerican Seed Co. 622 Town Road, West Chicago, Ill. 60185) were treated with ethyl methanesulfonate (EMS, commercially available from Sigma Chemical Co., St. Louis, Mo. 63178). Approximately 2,500 seeds were added to 400 ml of 0.4% (v/v) or 0.8% (v/v) EMS and were stirred gently for eight hours at ambient temperature. During a four-hour period following the EMS treatment, the seeds were washed sixteen times, each wash using continuous stirring with 400 ml distilled water. The treated seeds, identified as $M_1$ seeds, were then sown in trays containing soilless potting mix.

After several weeks, the seedlings were transplanted into pots containing soilless potting mix and maintained in the greenhouse. Flowers produced by those plants were naturally self-pollinated. The resulting seeds, identified as $M_2$ seeds, were harvested from approximately 2,300 plants. Of these 2,300 plants, approximately 1,500 were grown from seeds treated with 0.4% EMS and approximately 800 were grown from seeds treated with 0.8% EMS. To facilitate identification of mutant plants, the $M_2$ seeds from each of 50 $M_1$ plants were combined into one lot, resulting in a total of 47 seed lots. During the summer of the year 2000, 500 seeds from each of the 47 lots were sown and the resulting plants were field-grown at PanAmerican Seed Co. in Santa Paula, Calif. 93060.

EXAMPLE 2

HPLC Screening of EMS-Treated *Tagetes erecta* 'Scarletade'

EMS-treated 'Scarletade' plants were field-grown at PanAmerican Seed Co. in Santa Paula, Calif. 93060, and were screened by HPLC for altered zeaxanthin ratio. Flowers approximately 98% fully opened were selected for analysis. From each flower, one petal was removed one-third of the distance from the flower center and placed in a 3.5"×0.75" glass vial containing approximately 5 grams of glass beads. Vials were packaged with dry ice until stored at −80° C.

For analysis, solvent delivery and aliquot removal were accomplished with a robotic system comprising a single injector valve Gilson 232XL and a 402 2S1V diluter [Gilson, Inc. USA, 3000 W. Beltline Highway, Middleton, Wis.]. For saponification, 3 ml of 50% potassium hydroxide hydro-ethanolic solution (4 water:1 ethanol) was added to each vial, followed by the addition of 3 ml of octanol. The saponification treatment was conducted at room temperature with vials maintained on an IKA HS 501 horizontal shaker [Labworld-online, Inc. Wilmington, N.C.] for fifteen hours at 250 movements/minute, followed by a stationary phase of approximately one hour.

Following saponification, the supernatant was diluted with 0.9 ml of methanol. The addition of methanol was conducted under pressure to ensure sample homogeneity. Using a 0.25 ml syringe, a 0.1 ml aliquot was removed and transferred to HPLC vials for analysis.

For HPLC analysis, a Hewlett Packard 1100 HPLC, complete with a quaternary pump, vacuum degassing system, six-way injection valve, temperature regulated autosampler, column oven and Photodiode Array detector was used [Agilent Technologies available through Ultra Scientific Inc., 250 Smith Street, North Kingstown, R.I.]. The column was a Waters YMC 30, 5-micron, 4.6×250 mm with a guard column of the same material [Waters, 34 Maple Street, Milford, Mass.]. The solvents for the mobile phase were 81 methanol:4 water:15 tetrahydrofuran (THF) stabilized with 0.2% BHT (2,6-di-tert-butyl-4-methylphenol). Injections were 20 μl. Separation was isocratic at 30° C. with a flow rate of 1.7 ml/minute. The peak responses were measured by absorbance at 447 nm.

Using this protocol, the results from the first 2,546 samples were statistically analyzed to establish average values for lutein and zeaxanthin content. Because this was a semi-quantitative analytical screen, peak area values were used. To identify a mutant having a higher than average lutein and/or zeaxanthin concentration, a value of three standard deviations greater than the average was calculated. The calculated peak area means, standard deviations and zeaxanthin ratios are shown in Table 1, below.

TABLE 1

Lutein and Zeaxanthin Confidence Interval Calculations

| Statistic | Peak Area Lutein | Peak Area Zeaxanthin | Ratio (%) |
|---|---|---|---|
| Mean | 775.0 | 41.6 | 5.03 |
| Standard deviation (sd) | 263.2 | 16.4 | 0.71 |
| Mean + 3 sd | 1564.6 | 90.9 | 7.16 |

Based on the above values, samples were selected having lutein peak areas greater than 1565 and/or zeaxanthin peak areas greater than 91. Samples were also selected only for high lutein peak area, and for zeaxanthin ratios greater than 10 percent. A total of 88 mutants were identified from 21,754 assayed samples using these selection parameters. The total number of mutants resulting from each EMS seed treatment is shown in Table 2, below.

TABLE 2

Correlation of 'Scarletade' Mutants to EMS Treatment

| Selection Parameter | 0.4% EMS Treatment | 0.8% EMS Treatment | Total Plants |
|---|---|---|---|
| Zeaxanthin Ratio > 10% | 10 | 13 | 23 |
| Lutein > 1566 and Zeaxanthin > 91 | 18 | 10 | 28 |
| Lutein > 1566 and Zeaxanthin < 91 | 20 | 7 | 27 |
| Lutein < 1566 and Zeaxanthin > 91 | 7 | 3 | 10 |

More specific results of those assays as to relative levels of lutein and zeaxanthin are shown in Table 3, below.
Continuation of Table 3

TABLE 3

Identified 'Scarletade' Mutants

| Plant Identifier | Lutein Area | Zeaxanthin Area | Percent Zeaxanthin | Percent EMS Used |
|---|---|---|---|---|
| 124–257 | 2.115 | 55.635 | 96.34 | 0.4 |
| 119–494 | 9.254 | 131.036 | 93.40 | 0.8 |
| 112–263 | 8.095 | 35.273 | 81.33 | 0.4 |
| 118–036 | 11.441 | 31.691 | 73.47 | 0.8 |
| 088–452 | 2.94 | 6.689 | 69.47 | 0.4 |
| 118–035 | 11.289 | 23.951 | 67.97 | 0.8 |
| 114–334 | 58.24 | 97.968 | 62.72 | 0.4 |
| 117–185 | 39.002 | 44.027 | 53.03 | 0.8 |
| 108–108 | 13.424 | 10.155 | 43.07 | 0.4 |
| 088–425 | 8.959 | 4.394 | 32.91 | 0.4 |
| 094–238 | 7.285 | 3.063 | 29.60 | 0.4 |
| 110–308 | 46.753 | 14.248 | 23.36 | 0.4 |
| 132–346 | 31.036 | 8.856 | 22.20 | 0.8 |
| 100–334 | 282.987 | 54.298 | 16.10 | 0.8 |
| 101–331 | 246.402 | 46.467 | 15.87 | 0.8 |
| 100–198 | 119.381 | 21.449 | 15.23 | 0.8 |
| 101–190 | 139.027 | 23.125 | 14.26 | 0.8 |
| 114–315 | 351.524 | 56.898 | 13.93 | 0.4 |
| 100–470 | 189.703 | 27.743 | 12.76 | 0.8 |
| 117–348 | 369.903 | 43.315 | 10.48 | 0.8 |
| 132–266 | 374.096 | 43.8 | 10.48 | 0.8 |
| 123–310 | 60.743 | 6.818 | 10.09 | 0.4 |
| 116–106 | 453.538 | 50.287 | 9.98 | 0.8 |

About 21,700 plants exhibited typical zeaxanthin ratios of about 4 to about 7 percent (about 1:25 to about 1:15). The above data illustrate the relative rarity of the mutations contemplated, as well as the almost equal number of plants that exhibit reduced zeaxanthin levels. The data also do not show a preference for the use of one level of mutagen versus the other used here.

EXAMPLE 3

EMS Treatment of *Tagetes erecta* 13819

Seeds of *Tagetes erecta* xanthophyll marigold named 13819 (a proprietary breeding selection of PanAmerican Seed Co. 622 Town Road, West Chicago, Ill. 60185) were treated with ethyl methanesulfonate (EMS, commercially available from Sigma Chemical Co. St. Louis, Mo. 63178). Approximately, 7,000 seeds were added to 600 ml of 0.2% (v/v) or 0.4% (v/v) EMS and stirred gently for eight hours at ambient temperature. During a four-hour period following the EMS treatment, the seeds were washed sixteen times, each wash using continuous stirring with 600 ml distilled water.

The treated seeds, identified as $M_1$ seeds, were then sown in trays containing soilless potting mix. After three to four weeks, the seedlings were transplanted into the field. Flowers produced by these plants were bagged to prevent cross-pollination, and were permitted to spontaneously self-pollinate. The resulting seeds, identified as $M_2$ seeds, were harvested from approximately 2,391 plants. Of these plants, approximately 951 were grown from seeds treated with 0.2% EMS and approximately 1,440 were grown from seeds treated with 0.4% EMS.

To facilitate identification of mutant plants, the $M_2$ seeds from each of 50 plants were combined into one lot. This grouping resulted in a total of 48 seed lots. From late October through mid-November of the year 2000, 1000 seeds from each of 15 lots of the 0.4% EMS treatment were sown and 700 plants of each lot were greenhouse-grown at Seaview Nursery in El Rio, Calif. 93060. In addition, 1,500 seeds from all of the 48 lots were sown in late October of the year 2000, and 765 plants from each of the lots were field-grown at Semillas Pan American Chile LTDA, in Pichidegua, Chile.

EXAMPLE 4

HPLC Screening of EMS-Treated *Tagetes erecta* 13819

EMS-treated 13819 $M_2$ plants were greenhouse-grown at Seaview Nursery in El Rio, Calif. 93060 and field-grown at Semillas PanAmerican Chile LTDA, in Pichidegua, Chile, and were screened for altered zeaxanthin ratio. Flowers approximately 98% fully opened were selected for analysis. From these flowers, petals were removed one-third of the distance from the flower center. Approximately 100 mg of petal tissue was placed in plastic bags and stored frozen until analysis. Dry weight was determined for two petals that were placed in 3.5"×0.75" glass vials containing approximately 5 grams of glass beads.

For analysis, solvent delivery and aliquot removal were accomplished with a robotic system comprising a single injector valve Gilson 232XL and a 402 2S1V diluter. For saponification, 3 ml of 50% potassium hydroxide hydro-ethanolic solution (4 water: 1 ethanol) was added to each vial, followed by the addition of 3 ml octanol. The saponification treatment was conducted at room temperature with vials maintained on an IKA HS 501 horizontal shaker for fifteen hours at 250 movements per minute followed by a stationary phase of approximately one hour.

Following saponification, the supernatant was diluted with 0.9 ml of methanol. The addition of methanol was conducted under pressure to ensure sample homogeneity. Using a 0.25 ml syringe, a 0.1 ml aliquot was removed and transferred to HPLC vials for analysis.

For HPLC analysis, a Hewlett Packard 1100 complete with a quaternary pump, vacuum degassing system, six-way injection valve, temperature regulated autosampler, column oven and Photodiode Array detector was used. The column was a Waters YMC 30, 5-micron, 4.6×250 mm with a guard column of the same material. Standards were obtained from DHI—Water & Environment, DK—2970 Horsholm, Denmark and Sigma Chemical Co., St. Louis, Mo. 63178. The solvents for the mobile phase were 81 methanol:4 water:15 tetrahydrofuran stabilized with 0.2% BHT. Injections were 20 µl. Separation was isocratic at 30° C. with a flow rate of 1.7 ml/minute. The peak responses were measured at 447 nm.

Using this protocol, the results from the first 507 samples were statistically analyzed to establish average values for lutein and zeaxanthin content. To identify a mutant having a higher or lower than average lutein and zeaxanthin concentration, a value of three standard deviations greater than or less than the average was calculated. The calculated means, standard deviations and zeaxanthin ratios are shown in Table 4, below.

TABLE 4

Lutein and Zeaxanthin Confidence Interval Calculations

| Statistic | Lutein mg/g Fresh Weight | Zeaxanthin mg/g Fresh Weight | Lutein + Zeaxanthin mg/g Fresh Weight | Ratio (%) |
|---|---|---|---|---|
| Mean | 0.64 | 0.04 | 0.68 | 5.98 |
| Standard deviation | 0.14 | 0.01 | 0.147 | 1.1 |
| Mean + 3 sd | 1.06 | 0.07 | 1.12 | 9.28 |
| Mean − 3 sd | 0.22 | 0.007 | 0.24 | 2.68 |

Based on the above values, samples were selected having zeaxanthin ratios greater than 10 percent, combined lutein and zeaxanthin content greater than 1.12 mg/g fresh weight and combined lutein and zeaxanthin content less than 0.24 mg/g fresh weight. A total of 347 mutants were identified having a sum of lutein plus zeaxanthin greater than 1.12 mg/g, and 43 mutants having a zeaxanthin ratio greater than 10 percent were identified from 8192 samples using these selection parameters. The total number of mutants resulting from each EMS seed treatment is shown in Table 5, below.

TABLE 5

Correlation of 13819 Mutants to EMS Treatment

| Selection Parameter | 0.2% EMS Treatment | 0.4% EMS Treatment | Total Plants |
|---|---|---|---|
| Zeaxanthin Ratio > 10% | 2 | 41 | 43 |
| Lutein + Zeaxanthin > 1.12 mg/g dry weight | 6 | 341 | 347 |
| Lutein + Zeaxanthin < 0.24 mg/g dry weight | 2 | 175 | 177 |

Of the mutants having a zeaxanthin ratio greater than about 10 percent zeaxanthin, about 47 percent had between 10 and under 13 percent, whereas 53 percent exhibited 13 percent or greater.

EXAMPLE 5

Carotenoid Composition in Petals of Select Marigolds

Carotenoid compositions were determined for 'Scarletade' wild-type and mutant samples selected from those identified in the screening procedure described in Example 2. Petal samples were stored in a −80° C. freezer until mutants were identified. Samples were lyophilized, and the dried tissue was stored under argon at −80° C. until ready for analysis.

Extraction procedures were performed under red light. Dried petals were ground to pass through a No. 40 sieve mesh size. A ground sample was accurately weighed and transferred into a 100 ml red volumetric flask. To the sample, 500 microliters (µl) of $H_2O$ were added, and the mixture was swirled for 1 minute. Thirty ml of extractant solvent (10 ml hexane+7 ml acetone+6 ml absolute alcohol+7 ml toluene) were added, and the flask was shaken at 160 rpm for 10 minutes.

For saponification, 2 ml of 40% methanolic KOH were added into the flask, which was then swirled for one minute. The flask was placed in a 56° C. $H_2O$ bath for 20 minutes. An air condenser was attached to prevent loss of solvent. The sample was cooled in the dark for one hour with the condenser attached. After cooling, 30 ml of hexane were added, and the flask was shaken at 160 rpm for 10 minutes.

The shaken sample was diluted to volume (100 ml) with 10% sodium sulfate solution and shaken vigorously for one minute. The sample remained in the dark for at least 30 minutes. A 35 ml aliquot was removed from the approximately 50 ml upper phase, and transferred to a sample cup. An additional 30 ml of hexane were added into the flask that was then shaken at 160 rpm for 10 minutes. After approximately one hour, the upper phases were combined. For HPLC analysis, 10 ml aliquots were dried under nitrogen and stored under argon at −80° C.

HPLC equipment comprised an Alliance 2690 equipped with a refrigerated autosampler, column heater and a Waters Photodiode Array 996 detector (Waters Corp., 34 Maple Street Milford, Mass. 01757). Separation was obtained with a YMC $C_{30}$ column, 3 µm, 2.0×150 mm with a guard column of the same material. Standards were obtained from ICC Indofine Chemicals Somerville, N.J. 088876 and from DHI-Water & Environment, DK-2970 Horsholm, Denmark.

The dried mutant samples were resuspended in tetrahydrofuran and methanol to a total volume of 200 µl and filtered, whereas the control was not additionally concentrated. Carotenoids were separated using a gradient method. Initial gradient conditions were 90% methanol:5% water:5% methyl tert-butyl ether at a flow rate of 0.4 milliliters per minute (ml/min). From zero to 15 minutes, the mobile phase was changed from the initial conditions to 80 methanol:5 water:15 methyl tert-butyl ether, and from 15 to 60 minutes to 20 methanol:5 water:75 methyl tert-butyl ether. For the following 10 minutes, the mobile phase was returned to the initial conditions and the column equilibrated for an additional 10 minutes. The column temperature was maintained at 27° C. and the flow rate was 0.4 ml/minute. Injections were 10 µl. The majority of peak responses were measured at 450 nm and additional areas added from 286, 348, 400 and 472 nm extracted channels.

Values for carotenoid profiles of selected mutants are indicated in Tables 6a, 6b and 6c, below, using peak area as percent of the total area. Indicated compound identifications are based on spectra extracted and maximal absorbance in ethanol (lambda maxima; ETOH) obtained for major peaks in each chromatogram, some of which were verified by retention times of known standards. Values combine suspected isomers of the same compounds. Some compounds may contain minor impurities. Included in the Table are values for yellow colored American marigolds (yellow marigold) noted in Quackenbush et al., *J. Assoc. Off. Anal. Chem.*, 55(3): 617–621 (1972). Single entries are used in Tables 6a–6c for neoxanthin/violaxanthin and chrysanthemaxanthin/flavoxanthin compound pairs that could not be separated by the procedure used here.

TABLE 6a

Relative Percent Distribution of Carotenoids
In Petals of *Tagetes erecta* and Mutants

| Carotenoid | Wavelength in EtOH (nm) | Marigold Selections | | | | | | | | | |
|---|---|---|---|---|---|---|---|---|---|---|---|
| | | Yellow Marigold | 'Scarletade' | 13819 | 117–185 | 124–257 | 119–494 | 112–263 | 118–035 | 088–425 | 325–444 |
| Phytoene | 276, 286, 297 | 2.4 | 0.3 | 0.3 | 6.8 | 7.0 | 1.0 | 11.0 | 12.3 | 34.3 | 30.9 |
| Phytofluene (isomers) | 331, 348, 367 | 2.6 | 0.5 | 0.4 | 4.0 | 4.2 | 0.9 | 7.5 | 7.4 | 17.8 | 13.3 |
| ζ-Carotene (cis/trans isomers) | 377, 399, 425 | nf* | <0.1 | <0.1 | 5.6 | 5.3 | 1.3 | 6.9 | 6.8 | 18.2 | 17.1 |
| Neurosporene | 416, 440, 470 | nr** | <0.1 | <0.1 | 0.1 | 0.2 | <0.1 | <0.1 | <0.1 | 3.5 | 3.5 |
| Lycopene | 447, 472, 504 | nr | <0.1 | <0.1 | 0.5 | 1.3 | <0.1 | <0.1 | <0.1 | 1.0 | 2.8 |
| α-Carotene | 423, 444, 473 | 0.1 | <0.1 | <0.1 | <0.1 | <0.1 | <0.1 | <0.1 | <0.1 | 0.8 | 1.2 |
| β-Carotene | 425, 451, 478 | 0.5 | <0.1 | <0.1 | 4.4 | 6.8 | 2.3 | 0.6 | 0.3 | 2.3 | 4.8 |
| Neoxanthin | 415, 439, 467 | 0.8 | 1.5 | 4.1 | 13.3 | 12.8 | 16.7 | 4.3 | 3.5 | 0.7 | 1.1 |
| Violaxanthin | 419, 440, 470 | nr | | | | | | | | | |
| Antheraxanthin | 422, 444, 472 | 0.1 | 3.1 | 5.5 | 12.5 | 14.4 | 19.2 | 4.1 | 4.5 | 0.9 | 1.5 |
| Lutein | 420, 445, 475 | 72.3 | 84.9 | 81.7 | 13.3 | 1.3 | <0.1 | 0.6 | 7.1 | 2.0 | 4.9 |
| Zeaxanthin | 428, 450, 478 | 16.4 | 4.7 | 5.9 | 21.3 | 30.6 | 35.7 | 16.5 | 18.2 | 2.0 | 4.0 |
| α-Cryptoxanthin | 421, 446, 475 | 0.8 | <0.1 | <0.1 | <0.1 | <0.1 | <0.1 | 32.2 | 26.9 | <0.1 | 0.2 |
| β-Cryptoxanthin | 428, 450, 478 | 0.5 | <0.1 | <0.1 | 0.5 | 0.6 | 0.8 | 0.2 | 0.4 | 1.9 | 1.8 |
| β-Zeacarotene | 406, 428, 454 | 0.5 | | | | not identified | | | | | |
| Chrysanthemaxanthin | 400, 421, 448 | 0.8 | <0.1 | <0.1 | 2.3 | 1.5 | 4.5 | 0.8 | 0.5 | 0.2 | 0.2 |
| Flavoxanthin | 400, 421, 448 | 1.3 | | | | | | | | | |
| Auroxanthin | 380, 401, 426 | 0.1 | | | | not identified | | | | | |
| Other compounds that show absorbance at 450 nm | | 0.8 | 5.0 | 2.1 | 15.3 | 14.0 | 17.6 | 15.1 | 12.0 | 14.3 | 12.7 |

*nf = not found
**nr = not reported

TABLE 6b

Relative Percent Distribution of Carotenoids
In Petals of *Tagetes erecta* and Mutants

| Carotenoid | Wavelength in EtOH (nm) | Marigold Selections | | | | | | | |
|---|---|---|---|---|---|---|---|---|---|
| | | Yellow Marigold | 'Scarletade' | 13819 | 100–198 | 100–334 | 100–470 | 101–190 | 114–315 |
| Phytoene (isomers) | 276, 286, 297 | 2.4 | 0.3 | 0.3 | 4.8 | 3.9 | 6.1 | 3.4 | 5.2 |
| Phytofluene (isomers) | 331, 348, 367 | 2.6 | 0.5 | 0.4 | 3.2 | 3.2 | 3.8 | 3.2 | 3.3 |

TABLE 6b-continued

Relative Percent Distribution of Carotenoids
In Petals of *Tagetes erecta* and Mutants

| Carotenoid | Wave-length in EtOH (nm) | Yellow Marigold | 'Scarletade' | 13819 | 100–198 | 100–334 | 100–470 | 101–190 | 114–315 |
|---|---|---|---|---|---|---|---|---|---|
| ζ-Carotene (cis/trans isomers) | 377, 399, 425 | nf* | <0.1 | <0.1 | 4.8 | 4.0 | 4.4 | 3.6 | 3.2 |
| Neurosporene | 416, 440, 470 | nr** | <0.1 | <0.1 | <0.1 | <0.1 | <0.1 | <0.1 | <0.1 |
| Lycopene | 447, 472, 504 | nr | <0.1 | <0.1 | <0.1 | <0.1 | <0.1 | <0.1 | <0.1 |
| α-Carotene | 423, 444, 473 | 0.1 | <0.1 | <0.1 | 0.3 | 0.4 | 0.2 | 0.4 | 0.2 |
| β-Carotene | 425, 451, 478 | 0.5 | <0.1 | <0.1 | 0.8 | 0.7 | 0.5 | 0.8 | 0.5 |
| Neoxanthin | 415, 439, 467 | 0.8 | 1.5 | 4.1 | <0.2 | 0.3 | <0.2 | <0.2 | <0.2 |
| Violaxanthin | 419, 440, 470 | nr | | | | | | | |
| Anthera-xanthin | 422, 444, 472 | 0.1 | 3.1 | 5.5 | <0.2 | <0.2 | <0.2 | <0.2 | <0.2 |
| Lutein | 420, 445, 475 | 72.3 | 84.9 | 81.7 | 68.0 | 70.7 | 67.5 | 71.1 | 71.6 |
| Zeaxanthin | 428, 450, 478 | 16.4 | 4.7 | 5.9 | 14.8 | 13.4 | 13.1 | 13.6 | 12.3 |
| α-Crypto-xanthin | 421, 446, 475 | 0.8 | <0.1 | <0.1 | 0.6 | 0.6 | 0.5 | 0.6 | 0.4 |
| δ-Carotene | 431, 456, 489 | nr | <0.1 | <0.1 | 0.5 | 0.2 | 0.8 | 0.4 | 0.5 |
| β-Crypto-xanthin | 428, 450, 478 | 0.5 | <0.1 | <0.1 | <0.2 | <0.2 | <0.2 | <0.2 | <0.2 |
| β-Zeacarotene | 406, 428, 454 | 0.5 | | | | not identified | | | |
| Chrysanthema-xanthin | 400, 421, 448 | 0.8 | <0.1 | <0.1 | <0.2 | <0.2 | <0.2 | <0.2 | <0.2 |
| Flavoxanthin | 400, 421, 448 | 1.3 | | | | | | | |
| Auroxanthin | 380, 401, 426 | 0.1 | | | | not identified | | | |
| Other compounds that show absorbance at 450 nm | | 0.8 | 5.0 | 2.1 | 2.1 | 2.6 | 2.9 | 2.8 | 2.7 |

*nf = not found
**nr = not reported

TABLE 6c

Relative Percent Distribution of Carotenoids
In Petals of *Tagetes erecta* and Mutants

| Carotenoid | Wave-length in EtOH (nm) | Yellow Marigold | 'Scarletade' | 13819 | 126–415 | 098–240 | 098–394 | 115–004 |
|---|---|---|---|---|---|---|---|---|
| Phytoene (isomers) | 276, 286, 297 | 2.4 | 0.3 | 0.3 | 11.8 | 10.0 | 8.6 | 13.0 |
| Phytofluene (isomers) | 331, 348, 367 | 2.6 | 0.5 | 0.4 | 9.1 | 5.8 | 5.4 | 9.6 |
| ζ-Carotene (cis/trans isomers) | 377, 399, 425 | nf* | <0.1 | <0.1 | 5.0 | 3.6 | 3.5 | 10.3 |
| Neurosporene | 416, 440, 470 | nr** | <0.1 | <0.1 | <0.1 | <0.1 | <0.1 | <0.1 |
| Lycopene | 447, 472, 504 | nr | <0.1 | <0.1 | <0.1 | <0.1 | <0.1 | <0.1 |
| α-Carotene | 423, 444, 473 | nr | <0.1 | <0.1 | 0.5 | 0.4 | 0.4 | 0.6 |
| β-Carotene | 425, 451, 478 | 0.5 | <0.1 | <0.1 | 0.1 | 0.1 | 0.1 | <0.1 |
| Neoxanthin | 415, 439, 467 | 0.8 | 1.5 | 4.1 | 0.3 | 0.4 | 0.4 | <0.1 |

TABLE 6c-continued

Relative Percent Distribution of Carotenoids In Petals of *Tagetes erecta* and Mutants

| Carotenoid | Wavelength in EtOH (nm) | Yellow Marigold | 'Scarletade' | 13819 | 126–415 | 098–240 | 098–394 | 115–004 |
|---|---|---|---|---|---|---|---|---|
| Violaxanthin | 419, 440, 470 | nr | | | | | | |
| Antheraxanthin | 422, 444, 472 | 0.1 | 3.1 | 5.5 | 1.7 | 1.9 | 2.2 | 1.9 |
| Lutein | 420, 445, 475 | 72.3 | 84.9 | 81.7 | 61.7 | 70.1 | 71.0 | 52.3 |
| Zeaxanthin | 428, 450, 478 | 16.4 | 4.7 | 5.9 | 2.5 | 2.8 | 3.4 | 1.8 |
| α-Cryptoxanthin | 421, 446, 475 | 0.8 | <0.1 | <0.1 | 0.7 | 0.6 | 0.4 | 0.2 |
| δ-Carotene | 431, 456, 489 | nr | <0.1 | <0.1 | 1.6 | 0.4 | 0.3 | 5.2 |
| β-Cryptoxanthin | 428, 450, 478 | 0.1 | <0.1 | <0.1 | <0.1 | <0.1 | <0.1 | <0.1 |
| β-Zeacarotene | 406, 428, 454 | 0.5 | | | not identified | | | |
| Chrysanthemaxanthin | 400, 421, 448 | 0.8 | <0.1 | <0.1 | <0.1 | 0.1 | 0.1 | <0.1 |
| Flavoxanthin | 400, 421, 448 | 1.4 | | | | | | |
| Auroxanthin | 380, 401, 426 | 0.1 | | | not identified | | | |
| Other compounds that show absorbance at 450 nm | | 0.8 | 5.0 | 2.1 | 4.9 | 3.7 | 4.19 | 4.8 |

*nf = not found
**nr = not reported

EXAMPLE 6

Carotenoid Composition In Leaves of Select Marigolds

Leaves of several marigold plants were assayed for the relative concentration of colored carotenoids present. Leaves from 'Scarletade' and 13819 were used as controls for comparison to leaves from mutant plants. Assays were conducted as in Example 5 and are shown in Tables 7a and 7b, below, where single entries are used for neoxanthin/violaxanthin and chrysanthemaxanthin/flavoxanthin compound pairs that could not be separated. Data in Tables 7a and 7b were collected from different groups of plants grown under different conditions.

TABLE 7a

Relative Percent Distribution of Carotenoids in Leaves of *Tagetes erecta* and Mutants

| Carotenoid | Wavelength in EtOH (nm) | 'Scarletade' | 13819 | 124–257 | 119–494 | 117–185 | 086–013 |
|---|---|---|---|---|---|---|---|
| Phytoene | 276, 286, 297 | 0.1 | 0.4 | 0.5 | 0.2 | 0.2 | 0.5 |
| Neoxanthin | 415, 439, 467 | 9.2 | 17.6 | 36.3 | 22.7 | 26.8 | 11.6 |
| Violaxanthin | 419, 440, 470 | | | | | | |
| Antheraxanthin | 422, 444, 472 | 2.8 | 4.3 | 8.4 | 7.7 | 9.1 | 2.9 |
| Lutein | 420, 445, 475 | 44.3 | 37.8 | 0.5 | <0.1 | 1.6 | 34.0 |
| Zeaxanthin | 428, 450, 478 | 6.6 | 3.8 | 4.6 | 27.5 | 10.6 | 4.1 |
| β-Carotene | 425, 451, 478 | 22.6 | 26.5 | 34.1 | 25.0 | 32.7 | 35.8 |
| α-Carotene | 423, 444, 473 | 0.5 | 0.3 | <0.1 | <0.1 | <0.1 | 0.2 |
| Chrysanthemaxanthin | 400, 421, 448 | 1.1 | 1.0 | 0.9 | 4.1 | 3.2 | 0.5 |

TABLE 7a-continued

Relative Percent Distribution of Carotenoids
in Leaves of *Tagetes erecta* and Mutants

| Carotenoid | Wavelength in EtOH (nm) | Marigold Selections | | | | | |
|---|---|---|---|---|---|---|---|
| | | 'Scarletade' | 13819 | 124–257 | 119–494 | 117–185 | 086–013 |
| Flavoxanthin | 400, 421, 448 | | | | | | |
| Other compounds that show absorbance at 450 nm | | 12.8 | 8.3 | 14.7 | 12.7 | 15.8 | 10.4 |

TABLE 7b

Relative Percent Distribution of Carotenoids
in Leaves of *Tagetes erecta* and Mutants

| Carotenoid | Wavelength in EtOH (nm) | Marigold Selections | | | | | |
|---|---|---|---|---|---|---|---|
| | | 'Scarletade' | 100–198 | 100–334 | 100–470 | 101–190 | 114–315 |
| Phytoene | 276, 286, 297 | Inadequate Peak Separation | | | | | |
| Neoxanthin | 415, 439, 467 | 20.4 | <0.1 | 0.3 | <0.1 | 3.1 | <0.1 |
| Violaxanthin | 419, 440, 470 | | | | | | |
| Antheraxanthin | 422, 444, 472 | 1.6 | 1.7 | 1.8 | 1.6 | 5.4 | 1.1 |
| Lutein | 420, 445, 475 | 48.3 | 24.7 | 27.6 | 28.8 | 27.7 | 24.3 |
| Zeaxanthin | 428, 450, 478 | 0.4 | 46.3 | 43.1 | 44.0 | 32.3 | 48.2 |
| β-Carotene | 425, 451, 478 | 15.9 | 14.5 | 17.3 | 14.5 | 19.6 | 13.8 |
| α-Carotene | 423, 444, 473 | <0.1 | <0.1 | <0.1 | <0.1 | <0.1 | <0.1 |
| Chrysanthemaxanthin | 400, 421, 448 | 1.0 | <0.1 | <0.1 | <0.1 | <0.1 | <0.1 |
| Flavoxanthin | 400, 421, 448 | | | | | | |
| β-Cryptoxanthin | 428, 450, 478 | 0.3 | 0.3 | 0.3 | 0.6 | 0.3 | 0.9 |
| Other compounds that show absorbance at 450 nm | | 12.1 | 12.4 | 9.5 | 10.5 | 11.5 | 11.7 |

EXAMPLE 7

Preparation of Marigolds with Little Lutein and High Zeaxanthin, Phytoene, Lycopene or β-Carotene Levels Through Breeding of Mutants Marigold mutant selection 124–257 that exhibits an increased zeaxanthin to lutein ratio compared to wild type was selfed and the resulting seed was maintained. Plants from the selfing of marigold selection 124–257 were used as male parents in a cross with female parent PanAmerican Seed proprietary breeding line F9 Ap(85368-4). From this cross, $F_1$ plants were produced and selfed to yield an $F_2$ population.

Fifteen seedlings from the $F_2$ cross were analyzed for the absence of lutein using thin layer chromatography (TLC). Approximately 50 mg of fresh leaf tissue from each seedling was weighed into a 100×13 mm screw top tube containing five glass beads. Sealed vials were stored at −20° C.

For analysis, 500 µl of extractant solvent (10 ml hexane+7 ml acetone+6 ml absolute alcohol+7 ml toluene) were added, and the sealed tubes were vortexed for a minimum of 45 minutes. After vortexing, the solution was transferred to a 4 ml amber vial and evaporated under nitrogen. Samples were resuspended in 125 µl of the above-described extraction solvent and 10 µl were spotted on 19 channel silica gel plates. Plates were dried for approximately 10 minutes then developed for 25 minutes in a two channel 25 cm developing tank containing 100 ml of a 2:1 ethyl acetate: hexane solution. Upon removal, samples were evaluated for the absence of lutein.

From this screen, $F_2$ marigold selection 14649-3 was identified. This selection was used as the female parent in crosses with mutants 101–190 and 100–198, which exhibit an increased zeaxanthin to lutein ratio in addition to having reduced epoxycarotenoid (e.g., neoxanthin and violaxanthin) production compared to wild type.

Marigold mutant selection 100–198 was selfed and the resulting seed was maintained. Plants from the selfing of marigold selection 100–198 were used as the male parent in a cross with the female parent selection 14649-3 described above. From this cross, $F_1$ seeds were collected, and of these 30 seeds were planted. Eleven of the resulting plants were selfed. From this cross, $F_2$ seeds were collected, and 400 of those seeds were planted and grown.

TLC analysis, as described above, was used to analyze leaves of 151 seedlings. Thirty-two plants were identified based on reduced epoxycarotenoid production typical of mutant selection 100–198. The remaining TLC extract was analyzed using high performance liquid chromatography (HPLC), performed using a modified Example 5 protocol. Modifications include the following: dried samples were resuspended into methyl tert-butyl ether and methanol, all gradient conditions used water increased to 6% with a corresponding 1% decrease in methanol, and column temperature was maintained at 25° C.

Analysis confirmed that seven of the 32 plants exhibited an increased zeaxanthin to lutein ratio typical of mutant selection 124–257. Petal and leaf samples of the seven selections were extracted and analyzed according to the protocol in Example 5 with modifications noted above. The results for petals are shown in Table 8a, below, and results for leaves are shown in Table 9a thereafter. In addition, non-saponified petal samples were analyzed to determine the percentage, if any, of non-esterified zeaxanthin. Those data are presented in Table 10.

Marigold mutant selection 101–190 was selfed and the resulting seed was maintained. Marigold selection 101–190 was used as the male parent in a cross with the female parent selection 14649-3 described above. From this cross, $F_1$ seeds were collected and of those seeds, 30 were planted. Six of the resulting plants were selfed. From this latter cross, $F_2$ seeds were collected, planted and grown.

It was determined that the current TLC analysis method was inconclusive for this population. Therefore, approximately 30 plants were selected for HPLC analysis based on having an orange-colored sepal phenotype.

Samples were extracted as for TLC; however, HPLC analysis was conducted. Ten of the 30 selections were found to have reduced epoxy-carotenoid production typical of mutant selection 101–190 in addition to having an increased zeaxanthin to lutein ratio typical of selection 124–257.

Petal and leaf samples of the ten selections were extracted and analyzed according to the protocol in Example 5 with modifications noted above. The results for petals are shown in Tables 8b and 8c, and results for leaves are shown in Tables 9b and 9c. In addition, non-saponified petal samples were analyzed to determine the percentage of non-esterified zeaxanthin. Those data are presented in Table 10.

TABLE 8a

Relative Percent Distribution of Carotenoids In Petals of *Tagetes erecta* and Mutant Crosses

| Carotenoid | Wavelength in EtOH (nm) | 'Scarletade' | 124–257 | 100–198 | 27772–029 | 27772–036 | 27772–100 | 27772–109 | 27772–123 | 27772–130 | 27772–134 |
|---|---|---|---|---|---|---|---|---|---|---|---|
| Phytoene (isomers) | 276, 286, 297 | 0.5 | 3.9 | 4.5 | 4.9 | 9.2 | 7.0 | 5.1 | 5.6 | 5.7 | 11.7 |
| Phytofluene (isomers) | 331, 348, 367 | 0.7 | 3.6 | 4.4 | 4.6 | 7.2 | 5.7 | 4.6 | 5.3 | 5.0 | 8.2 |
| ζ-Carotene (cis/trans isomers) | 377, 399, 425 | <0.2 | 3.3 | 4.1 | 4.8 | 10.6 | 5.2 | 4.5 | 5.0 | 4.4 | 7.4 |
| Neurosporene | 416, 440, 470 | <0.2 | <0.2 | <0.2 | 0.2 | 0.4 | 0.3 | <0.2 | 0.2 | 0.3 | 0.4 |
| Lycopene | 447, 472, 504 | <0.2 | 0.5 | <0.2 | 0.3 | 1.4 | 0.9 | <0.2 | 0.6 | 0.3 | 0.9 |
| α-Carotene | 423, 444, 473 | <0.2 | <0.2 | 0.4 | <0.2 | <0.2 | <0.2 | <0.2 | <0.2 | <0.2 | <0.2 |
| β-Carotene | 425, 451, 478 | <0.2 | 7.4 | 1.3 | 6.3 | 6.1 | 4.9 | 4.5 | 4.2 | 5.0 | 4.8 |
| Neoxanthin | 415, 439, 467 | 0.5 | 3.4 | <0.2 | <0.2 | <0.2 | <0.2 | <0.2 | <0.2 | <0.2 | <0.2 |
| Violaxanthin | 419, 440, 470 | 0.7 | 12.7 | <0.2 | <0.2 | <0.2 | <0.2 | <0.2 | <0.2 | 0.2 | <0.2 |
| Antheraxanthin | 422, 444, 472 | 1.6 | 17.5 | 0.6 | 0.5 | 0.4 | 0.6 | 0.5 | 0.5 | 0.7 | 0.3 |
| Lutein | 420, 445, 475 | 91.0 | 2.3 | 68.1 | 0.5 | 0.5 | 0.5 | 0.4 | 0.4 | 0.6 | 0.4 |
| Zeaxanthin | 428, 450, 478 | 3.3 | 29.8 | 14.3 | 73.8 | 60.0 | 70.3 | 76.5 | 74.3 | 72.4 | 62.0 |
| α-Cryptoxanthin | 421, 446, 475 | <0.2 | <0.2 | <0.2 | <0.2 | <0.2 | <0.2 | <0.2 | <0.2 | <0.2 | <0.2 |
| δ-Carotene | 431, 456, 489 | <0.2 | <0.2 | 0.7 | <0.2 | <0.2 | <0.2 | <0.2 | <0.2 | 0.3 | <0.2 |
| β-Cryptoxanthin | 428, 450, 478 | <0.2 | 1.0 | <0.2 | 1.1 | 1.0 | 1.1 | 1.4 | 1.1 | 1.1 | 1.1 |
| β-Zeacarotene | 406, 428, 454 | | | | | not identified | | | | | |
| Chrysanthemaxanthin | 400, 421, 448 | <0.2 | 1.7 | <0.2 | <0.2 | <0.2 | <0.2 | <0.2 | <0.2 | <0.2 | <0.2 |
| Flavoxanthin | 400, 421, 448 | | | | | | | | | | |

TABLE 8a-continued

Relative Percent Distribution of Carotenoids
In Petals of *Tagetes erecta* and Mutant Crosses

| Carotenoid | Wave-length in EtOH (nm) | Marigold Selections | | | | | | | | | |
|---|---|---|---|---|---|---|---|---|---|---|---|
| | | 'Scarletade' | 124–257 | 100–198 | 27772–029 | 27772–036 | 27772–100 | 27772–109 | 27772–123 | 27772–130 | 27772–134 |
| Auroxanthin | 380, 401, 426 | | | | not identified | | | | | | |
| Other compounds that show absorbance at 450 nm | | 1.7 | 12.9 | 1.6 | 2.8 | 3.2 | 3.5 | 2.4 | 2.7 | 4.2 | 2.8 |

TABLE 8b

Relative Percent Distribution of Carotenoids
In Petals of *Tagetes erecta* and Mutant Crosses

| Carotenoid | Wave-length in EtOH (nm) | Marigold Selections | | | | | | | |
|---|---|---|---|---|---|---|---|---|---|
| | | 'Scarletade' | 124–257 | 101–190 | 27773–006 | 27773–030 | 27773–087 | 27773–107 | 27773–128 |
| Phytoene (isomers) | 276, 286, 297 | 0.5 | 3.9 | 3.9 | 3.2 | 5.9 | 6.8 | 8.3 | 4.9 |
| Phytofluene (isomers) | 331, 348, 367 | 0.7 | 3.6 | 4.6 | 3.8 | 5.8 | 7.2 | 7.3 | 4.9 |
| ζ-Carotene (cis/trans isomers) | 377, 399, 425 | <0.2 | 3.3 | 5.1 | 4.4 | 5.0 | 10.4 | 8.6 | 5.0 |
| Neurosporene | 416, 440, 470 | <0.2 | <0.2 | <0.2 | <0.2 | 0.2 | <0.2 | <0.2 | <0.2 |
| Lycopene | 447, 472, 504 | <0.2 | 0.5 | <0.2 | 0.2 | 0.4 | 0.8 | <0.2 | 0.4 |
| α-Carotene | 423, 444, 473 | <0.2 | <0.2 | 0.3 | <0.2 | <0.2 | <0.2 | <0.2 | <0.2 |
| β-Carotene | 425, 451, 478 | <0.2 | 7.4 | 1.6 | 9.8 | 8.9 | 11.7 | 8.0 | 7.1 |
| Neoxanthin | 415, 439, 467 | 0.5 | 3.4 | <0.2 | <0.2 | <0.2 | <0.2 | <0.2 | <0.2 |
| Violaxanthin | 419, 440, 470 | 0.7 | 12.7 | <0.2 | <0.2 | <0.2 | <0.2 | <0.2 | <0.2 |
| Antheraxanthin | 422, 444, 472 | 1.6 | 17.5 | 0.6 | 1.9 | 1.8 | 0.9 | 0.8 | 2.1 |
| Lutein | 420, 445, 475 | 91.0 | 2.3 | 63.8 | 0.8 | 0.6 | 0.9 | 0.7 | 0.6 |
| Zeaxanthin | 428, 450, 478 | 3.3 | 29.8 | 16.8 | 69.4 | 67.9 | 58.5 | 62.4 | 70.3 |
| α-Cryptoxanthin | 421, 446, 475 | <0.2 | <0.2 | <0.2 | <0.2 | <0.2 | <0.2 | <0.2 | <0.2 |
| δ-Carotene | 431, 456, 489 | <0.2 | <0.2 | 0.2 | 0.9 | <0.2 | 0.2 | 0.4 | <0.2 |
| β-Cryptoxanthin | 428, 450, 478 | <0.2 | 1.0 | 0.2 | 1.1 | 1.2 | 1.1 | 1.5 | 1.3 |
| β-Zeacarotene | 406, 428, 454 | | | | not identified | | | | |
| Chrysanthemaxanthin | 400, 421, 448 | <0.2 | 1.7 | <0.2 | <0.2 | <0.2 | <0.2 | <0.2 | <0.2 |
| Flavoxanthin | 400, 421, 448 | | | | | | | | |
| Auroxanthin | 380, 401, 426 | | | | not identified | | | | |
| Other compounds that show absorbance at 450 nm | | 1.7 | 12.9 | 2.8 | 4.1 | 2.2 | 1.5 | 1.7 | 3.2 |

TABLE 8c

Relative Percent Distribution of Carotenoids
in Petals of *Tagetes erecta* and Mutant Crosses

| Carotenoid | Wavelength in EtOH (nm) | Marigold Selections | | | | | | | |
|---|---|---|---|---|---|---|---|---|---|
| | | 'Scarletade' | 124–257 | 101–190 | 27774–008 | 27774–050 | 27774–064 | 27774–076 | 27774–123 |
| Phytoene (isomers) | 276, 286, 297 | 0.5 | 3.9 | 3.9 | 4.4 | 5.2 | 7.0 | 8.8 | 5.6 |
| Phytofluene (isomers) | 331, 348, 367 | 0.7 | 3.6 | 4.6 | 4.6 | 5.7 | 6.0 | 8.8 | 5.5 |
| ζ-Carotene (cis/trans isomers) | 377, 399, 425 | <0.2 | 3.3 | 5.1 | 4.2 | 8.5 | 6.0 | 9.8 | 5.9 |
| Neurosporene | 416, 440, 470 | <0.2 | <0.2 | <0.2 | 0.2 | <0.2 | 0.3 | 0.3 | <0.2 |
| Lycopene | 447, 472, 504 | <0.2 | 0.5 | <0.2 | 0.4 | 0.6 | 0.4 | 1.5 | 0.2 |
| α-Carotene | 423, 444, 473 | <0.2 | <0.2 | 0.3 | <0.2 | <0.2 | <0.2 | <0.2 | <0.2 |
| β-Carotene | 425, 451, 478 | <0.2 | 7.4 | 1.6 | 7.0 | 9.5 | 5.8 | 9.9 | 10.1 |
| Neoxanthin | 415, 439, 467 | 0.5 | 3.4 | <0.2 | <0.2 | <0.2 | <0.2 | <0.2 | <0.2 |
| Violaxanthin | 419, 440, 470 | 0.7 | 12.7 | <0.2 | <0.2 | <0.2 | <0.2 | <0.2 | <0.2 |
| Antheraxanthin | 422, 444, 472 | 1.6 | 17.5 | 0.6 | 2.5 | <0.2 | 1.5 | 1.9 | 2.5 |
| Lutein | 420, 445, 475 | 91.0 | 2.3 | 63.8 | 0.8 | 0.8 | 0.7 | 0.6 | 0.8 |
| Zeaxanthin | 428, 450, 478 | 3.3 | 29.8 | 16.8 | 71.2 | 66.9 | 67.8 | 54.3 | 64.3 |
| α-Cryptoxanthin | 421, 446, 475 | <0.2 | <0.2 | <0.2 | <0.2 | <0.2 | <0.2 | <0.2 | <0.2 |
| δ-Carotene | 431, 456, 489 | <0.2 | <0.2 | 0.2 | <0.2 | <0.2 | <0.2 | <0.2 | <0.2 |
| β-Cryptoxanthin | 428, 450, 478 | <0.2 | 1.0 | 0.2 | 1.1 | 1.0 | 1.6 | 1.3 | 1.3 |
| β-Zeacarotene | 406, 428, 454 | not identified | | | | | | | |
| Chrysanthemaxanthin | 400, 421, 448 | <0.2 | 1.7 | <0.2 | <0.2 | <0.2 | <0.2 | <0.2 | <0.2 |
| Flavoxanthin | 400, 421, 448 | | | | | | | | |
| Auroxanthin | 380, 401, 426 | not identified | | | | | | | |
| Other compounds that show absorbance at 450 nm | | 1.7 | 12.9 | 2.8 | 3.6 | 1.3 | 2.9 | 2.4 | 3.4 |

TABLE 9a

Relative Percent Distribution of Carotenoids
in Leaves of *Tagetes erecta* and Mutant Crosses

| Carotenoid | Wavelength in EtOH (nm) | Marigold Selections | | | | | | | | | |
|---|---|---|---|---|---|---|---|---|---|---|---|
| | | 'Scarletade' | 124–257 | 100–198 | 27772–029 | 27772–036 | 27772–100 | 27772–109 | 27772–123 | 27772–130 | 27772–134 |
| Phytoene | 276, 286, 297 | Inadequate Peak Separation | | | | | | | | | |
| Neoxanthin | 415, 439, 467 | 9.4 | 9.6 | 0.3 | <0.2 | <0.2 | <0.2 | <0.2 | <0.2 | <0.2 | <0.2 |
| Violaxanthin | 419, 440, 470 | 7.1 | 26.3 | 0.4 | <0.2 | <0.2 | <0.2 | <0.2 | <0.2 | <0.2 | <0.2 |
| Antheraxanthin | 422, 444, 472 | 1.1 | 7.7 | 2.6 | 1.7 | 1.8 | 3.1 | 3.4 | 2.5 | 2.2 | 1.5 |
| Lutein | 420, 445, 475 | 44.7 | 0.4 | 34.8 | <0.2 | <0.2 | <0.2 | <0.2 | <0.2 | <0.2 | <0.2 |
| Zeaxanthin | 428, 450, 478 | 0.3 | 4.8 | 29.6 | 59.1 | 59.9 | 59.0 | 61.4 | 60.4 | 61.1 | 67.0 |

TABLE 9a-continued

Relative Percent Distribution of Carotenoids
in Leaves of *Tagetes erecta* and Mutant Crosses

| Carotenoid | Wavelength in EtOH (nm) | 'Scarletade' | 124–257 | 100–198 | 27772–029 | 27772–036 | 27772–100 | 27772–109 | 27772–123 | 27772–130 | 27772–134 |
|---|---|---|---|---|---|---|---|---|---|---|---|
| β-Carotene | 425, 451, 478 | 26.9 | 37.9 | 22.1 | 29.0 | 28.4 | 28.5 | 28.0 | 29.6 | 28.2 | 24.3 |
| α-Carotene | 423, 444, 473 | 0.8 | <0.2 | 0.3 | <0.2 | <0.2 | <0.2 | <0.2 | 1.1 | <0.2 | <0.2 |
| Chrysanthemaxanthin | 400, 421, 448 | 0.7 | 1.5 | <0.2 | <0.2 | 0.6 | 0.4 | <0.2 | <0.2 | <0.2 | <0.2 |
| Flavoxanthin | 400, 421, 448 | | | | | | | | | | |
| β-Cryptoxanthin | 428, 450, 478 | 0.2 | 0.3 | 0.5 | <0.2 | 0.6 | <0.2 | 0.5 | <0.2 | <0.2 | 0.4 |
| Other compounds that show absorbance at 450 nm | | 8.8 | 11.5 | 9.4 | 10.2 | 8.7 | 9.0 | 6.8 | 6.4 | 8.6 | 6.9 |

TABLE 9b

Relative Percent Distribution of Carotenoids
in Leaves of *Tagetes erecta* and Mutant Crosses

| Carotenoid | Wavelength in EtOH (nm) | 'Scarletade' | 124–257 | 101–190 | 27773–006 | 27773–030 | 27773–087 | 27773–107 | 27773–128 |
|---|---|---|---|---|---|---|---|---|---|
| Phytoene | 276, 286, 297 | Inadequate Peak Separation | | | | | | | |
| Neoxanthin | 415, 439, 467 | 9.4 | 9.6 | 7.6 | 6.2 | 5.0 | 4.6 | 3.7 | 6.9 |
| Violaxanthin | 419, 440, 470 | 7.1 | 26.3 | 3.9 | 2.9 | 1.8 | 1.7 | 0.9 | 4.7 |
| Antheraxanthin | 422, 444, 472 | 1.1 | 7.7 | 7.9 | 8.7 | 8.1 | 6.6 | 6.6 | 13.9 |
| Lutein | 420, 445, 475 | 44.7 | 0.4 | 37.6 | 0.9 | 0.4 | <0.2 | 0.4 | 0.7 |
| Zeaxanthin | 428, 450, 478 | 0.3 | 4.8 | 9.2 | 43.2 | 44.9 | 47.8 | 48.5 | 30.3 |
| β-Carotene | 425, 451, 478 | 26.9 | 37.9 | 25.2 | 30.9 | 32.3 | 31.8 | 31.6 | 32.2 |
| α-Carotene | 423, 444, 473 | 0.8 | <0.2 | 0.5 | <0.2 | <0.2 | <0.2 | <0.2 | <0.2 |
| Chrysanthemaxanthin | 400, 421, 448 | 0.7 | 1.5 | <0.2 | <0.2 | <0.2 | <0.2 | <0.2 | 0.5 |
| Flavoxanthin | 400, 421, 448 | | | | | | | | |
| β-Cryptoxanthin | 428, 450, 478 | 0.2 | 0.3 | <0.2 | <0.2 | <0.2 | <0.2 | <0.2 | 0.7 |
| Other compounds that show absorbance at 450 nm | | 8.8 | 11.5 | 8.1 | 7.3 | 7.6 | 7.5 | 8.3 | 10.2 |

TABLE 9c

Relative Percent Distribution of Carotenoids in
Leaves of *Tagetes erecta* and Mutant Crosses

| Carotenoid | Wavelength in EtOH (nm) | 'Scarletade' | 124–257 | 101–190 | 27774–008 | 27774–050 | 27774–064 | 27774–076 | 27774–123 |
|---|---|---|---|---|---|---|---|---|---|
| Phytoene | 276, 286, 297 | Inadequate Peak Separation | | | | | | | |

TABLE 9c-continued

Relative Percent Distribution of Carotenoids in Leaves of *Tagetes erecta* and Mutant Crosses

| Carotenoid | Wavelength in EtOH (nm) | Marigold Selections | | | | | | | |
|---|---|---|---|---|---|---|---|---|---|
| | | 'Scarletade' | 124–257 | 101–190 | 27774–008 | 27774–050 | 27774–064 | 27774–076 | 27774–123 |
| Neoxanthin | 415, 439, 467 | 9.4 | 9.6 | 7.6 | 4.7 | 5.7 | 4.7 | 5.2 | 6.2 |
| Violaxanthin | 419, 440, 470 | 7.1 | 26.3 | 3.9 | 1.4 | 2.9 | 1.6 | 1.7 | 3.3 |
| Antheraxanthin | 422, 444, 472 | 1.1 | 7.7 | 7.9 | 7.4 | 11.4 | 7.2 | 7.8 | 11.7 |
| Lutein | 420, 445, 475 | 44.7 | 0.4 | 37.6 | 1.2 | 0.5 | 0.5 | 0.4 | 0.8 |
| Zeaxanthin | 428, 450, 478 | 0.3 | 4.8 | 9.2 | 48.2 | 41.5 | 49.0 | 48.3 | 40.5 |
| β-Carotene | 425, 451, 478 | 26.9 | 37.9 | 25.2 | 27.5 | 29.9 | 27.4 | 28.4 | 27.2 |
| α-Carotene | 423, 444, 473 | 0.8 | <0.2 | 0.5 | 1.1 | <0.2 | <0.2 | <0.2 | <0.2 |
| Chrysanthemaxanthin | 400, 421, 448 | 0.7 | 1.5 | <0.2 | 0.5 | 0.4 | 0.5 | <0.2 | 0.3 |
| Flavoxanthin | 400, 421, 448 | | | | | | | | |
| β-Cryptoxanthin | 428, 450, 478 | 0.2 | 0.3 | <0.2 | <0.2 | 0.5 | <0.2 | <0.2 | 0.5 |
| Other compounds that show absorbance at 450 nm | | 8.8 | 11.5 | 8.1 | 8.0 | 7.3 | 9.2 | 8.3 | 9.5 |

TABLE 10

Relative Percent Non-esterified Zeaxanthin In Petals of *Tagetes erecta* And Mutant Crosses

| Marigold Selection | % Non-esterified Zeaxanthin |
|---|---|
| 'Scarletade' | 0 |
| 124–257 | 1.1 |
| 100–198 | 2.2 |
| 101–190 | 1.6 |
| 27772–029 | 6.8 |
| 27772–036 | 5.8 |
| 27772–100 | 7.9 |
| 27772–109 | 13.0 |
| 27772–123 | 7.3 |
| 27772–130 | 6.4 |
| 27772–134 | 5.0 |
| 27773–006 | 8.1 |
| 27773–030 | 3.2 |
| 27773–087 | 13.6 |
| 27773–107 | 19.3 |
| 27773–128 | 7.4 |
| 27774–008 | 3.9 |
| 27774–050 | 9.1 |
| 27774–064 | 6.3 |
| 27774–076 | 4.5 |
| 27774–123 | 6.8 |

Mutant selection 119–494 (Table 6a), characterized as having an increased zeaxanthin to lutein ratio compared to wild type, was selfed and the resulting seed was maintained. Mutant selection 115–004 (Table 6c), characterized as having an increased phytoene to lutein ratio compared to wild type, was selfed and the resulting seed was maintained.

The selfed selection 115-004 was used as a female parent in a cross with male parent selfed 119-494. From this cross, $F_1$ plants were produced and selfed to yield an $F_2$ population. $F_2$ plants exhibiting increased lycopene isomer accumulation as compared to wild type *Tagetes erecta* were noted by their red color in a greenhouse planting. Analysis confirmed the lycopene accumulation as well as increased levels of phytoene and β-carotene. Samples were analyzed according to the HPLC protocol outlined above with the exception that a second hexane extraction was not performed. Data from six selections denominated 33457-1, 33458-1, 33459-1, 33456-2, 33458-2 and 33461-1 are reported in Table 11, below.

Additional lycopene, phytoene and β-carotene accumulators were subsequently noted. Selection 27774-105 was from the cross of female parent 14649-3 and male parent 101-190 (Table 8b) described in this Example. Petals were analyzed as described above and data are reported in Table 11.

Selection 23012-3 is an $F_3$ plant resulting from the cross of a large-double flower PanAmerican Seed proprietary breeding line 85394-2 as the female parent and 124–257 as the male parent. After selfing, an $F_2$ selection characterized as having reduced lutein level was identified by the TLC procedure and the resulting $F_3$ seed was sown in the field located at PanAmerican Seed Santa Paula, Calif. In this population selection 23012-3 was identified by its red colored petals. Petals were analyzed as described above and data are reported in Table 11.

TABLE 11

Relative Percent Distribution of Carotenoids
In Petals of *Tagetes erecta* And Mutants

| Carotenoid | Wavelength in EtOH (nm) | Marigold Selections | | | | | | | | |
|---|---|---|---|---|---|---|---|---|---|---|
| | | 'Scarletade' | 124-257 | 33457-1 | 33458-1 | 33459-1 | 33456-2 | 33458-2 | 33461-1 | 23012-3 | 27774-105 |
| Phytoene (isomers) | 276, 286, 297 | 0.5 | 3.9 | 25.7 | 15.9 | 24.7 | 16.8 | 17.0 | 14.9 | 10.5 | 8.6 |
| Phytofluene (isomers) | 331, 348, 367 | 0.7 | 3.6 | 15.4 | 8.6 | 14.3 | 13.6 | 13.1 | 11.4 | 5.8 | 8.4 |
| ζ-Carotene (cis/trans isomers) | 377, 399, 425 | <0.2 | 3.3 | 10.0 | 5.4 | 10.4 | 10.2 | 10.6 | 8.4 | 6.3 | 4.0 |
| Neurosporene | 416, 440, 470 | <0.2 | <0.2 | <0.2 | <0.2 | <0.2 | <0.2 | <0.2 | <0.2 | <0.2 | <0.2 |
| Lycopene | 447, 472, 504 | <0.2 | 0.5 | 3.5 | 3.2 | 3.9 | 5.6 | 6.3 | 8.5 | 13.6 | 6.8 |
| α-Carotene | 423, 444, 473 | <0.2 | <0.2 | <0.2 | <0.2 | <0.2 | <0.2 | <0.2 | <0.2 | <0.2 | <0.2 |
| β-Carotene | 425, 451, 478 | <0.2 | 7.4 | 3.8 | 3.8 | 3.8 | 16.1 | 12.4 | 9.8 | 9.9 | 10.5 |
| Neoxanthin | 415, 439, 467 | 0.5 | 3.4 | 2.0 | 3.0 | 3.3 | 3.1 | 2.9 | 4.1 | 1.3 | 1.2 |
| Violaxanthin | 419, 440, 470 | 0.7 | 12.7 | 4.4 | 9.6 | 4.4 | 4.0 | 4.7 | 5.4 | 5.9 | 4.0 |
| Antheraxanthin | 422, 444, 472 | 1.6 | 17.5 | 6.7 | 13.7 | 5.7 | 5.6 | 6.2 | 6.7 | 10.4 | 11.3 |
| Lutein | 420, 445, 475 | 91.0 | 2.3 | <0.2 | <0.2 | <0.2 | <0.2 | <0.2 | <0.2 | 2.1 | 1.7 |
| Zeaxanthin | 428, 450, 478 | 3.3 | 29.8 | 14.9 | 23.0 | 10.2 | 11.9 | 12.8 | 18.0 | 18.5 | 32.0 |
| α-Cryptoxanthin | 421, 446, 475 | <0.2 | <0.2 | <0.2 | <0.2 | <0.2 | <0.2 | <0.2 | <0.2 | <0.2 | <0.2 |
| δ-Carotene | 431, 456, 489 | <0.2 | <0.2 | <0.2 | <0.2 | <0.2 | <0.2 | <0.2 | <0.2 | <0.2 | <0.2 |
| β-Cryptoxanthin | 428, 450, 478 | <0.2 | 1.0 | 0.5 | 0.7 | 0.4 | 0.5 | 0.5 | 0.5 | 0.6 | 1.1 |
| β-Zeacarotene | 406, 428, 454 | | | | | not identified | | | | | |
| Chrysanthemaxanthin | 400, 421, 448 | <0.2 | 1.7 | 1.1 | 1.9 | 1.0 | 0.8 | 0.9 | 0.7 | 1.7 | 1.0 |
| Flavoxanthin | 400, 421, 448 | | | | | | | | | | |
| Auroxanthin | 380, 401, 426 | | | | | not identified | | | | | |
| Other compounds that show absorbance at 450 nm | | 1.7 | 12.9 | 12.1 | 11.2 | 17.9 | 11.7 | 12.8 | 11.7 | 13.3 | 9.4 |

*Certain peaks have not been characterized and a significant number of those listed above as well as other peaks may be lycopene isomers.

EXAMPLE 8

Alternate Methods for Creating Altered Carotenoid Profiles in *Tagetes erecta*

In addition to creating *Tagetes erecta* having altered carotenoid profiles through the use of chemical mutagenesis, alternative methods for providing an altered carotenoid profile can be utilized. Illustrative alternate methods include the use of ionizing radiation and gene silencing using recombinant DNA technology.

More specifically, ionizing radiation has been used to modify gene expression through deletion mutations. Gamma rays have been reported to modify flower color in ornamental species including *Dendranthema, Gladiolus* and *Zinnia* [See Datta et al., *Zeitschrift fur Pflanzen.*, 120(1):91–92 (2001); Masakazu, et al., *J. Japanese Soc. For Hort. Sci.*, 70(1): 126–128 (2001) and Venkatachalam et al., *Ind. Jour. Gen. & Plant Breed.*, 57(3):255–261 (1997)]. Fast neutrons have been effective in generating deletion mutations in plants. Thus, deletion mutants were obtained for 84% of targeted loci from a mutated Arabidopsis population of 51,840 plants [See Li et al., *The Plant Journal*, 27(3):235–242(2001).], whereas Love et al., *Amer. Soc. Hort. Sci.*, 88:627–630 (1966) prepared foliage anthocyanin mutations in Coleus. More recently, flower color mutants of Dahlia were reported [See Abe et al., *In Vitro Cell. & Dev. Bio.* 38:93A (2002)].

Gene silencing can also be used to inactivate targeted genes in order to prepare desirable phenotypes such as altered flower pigmentation profiles. Such methods include gene silencing at the transcriptional as well as posttranscriptional level.

Recombinantly-induced, stably integrated transgenes as well as replicating DNA and RNA viruses can mediate silencing events. Transcriptional gene silencing results from the impairment of transcription initiation through promoter methylation and/or chromatin condensation. Homozygous progeny of transgenic petunia containing a transgene for brick-red pelargonidin flower pigmentation unexpectedly yielded a white derivative having a hypermethylated CaMV 35S promoter [See Meyer et al., *Plant Journal* 4(1):89–100 (1993)].

Post-transcriptional gene silencing, in which transcription occurs but RNA fails to accumulate, results from the degradation of mRNA when aberrant sense, antisense, or double-stranded forms of RNA are produced. In petunia, a recombinantly-introduced, transcribed sense transgene encoding for the enzyme chalcone synthase of the flavonoid biosynthetic pathway could down-regulate the expression of homologous endogenous gene and transgene RNA, a phenomenon termed co-suppression. Instead of the expected increased production of the encoded enzyme, 42 percent of the transgenic plants had flowers that were white and/or patterned with white [See Napoli et al., *Plant Cell,* 2(4):279–289 (1990)].

Before the discovery of co-suppression, down-regulation of endogenous genes was achieved with antisense transgenes. A comparison of sense and antisense chalcone synthase transgenic Petunia identified 75% of the sense transgenics and 82% of the antisense transgenics as having altered flower pigmentation [See Jorgensen et al., *Plant Mol. Biol.*, 31(5):957–973 (1996)].

From double-stranded RNA, small interfering RNAs (siRNA) are processed, and these have been shown to be effective in silencing genes in plants [See Hamilton et al., *Science,* 286(5441):950–952 (1999)]. Intermediates of RNA degradation were identified in co-suppressed petunia plants [See Metzlaff et al., *Cell* 88(6):845–854 (1997)]. Transformation vectors that produced RNAs capable of duplex formation caused specific and heritable genetic interference of four flower- or meristem-related genes in *Arabidopsis thaliana* [See Chuang et al., *Proc. Natl. Acad. Sci.,* 97(9):4985–4990 (2000)].

In addition, post-transcriptional gene silencing can be accomplished through vectors engineered to express ribozymes capable of cleaving RNA. One class termed 'small ribozymes' includes hairpin ribozyme and hammerhead ribozyme. Efficient gene silencing was also demonstrated in a wide range of plant species using constructs encoding self-complementary hairpin RNA. Intron-containing constructs generally resulted in 90 to 100% of independent transgenics showing gene silencing [See Wesley et al., *Plant Journal,* 27(6):581–590 (2001)]. A transgenic potato plant expressing a hammerhead ribozyme directed against the potato spindle tuber viroid RNA showed high resistance against its replication. This resistance was stably inherited to progeny [See Yang et al., *Proc. Natl. Acad. Sci.,* 94:4861–4865 (1997)].

In the present invention, suitable recombinantly-provided transgenes for gene silencing include expression vectors containing one or more sequence(s) of a *Tagetes* plant encoding enzyme(s) necessary for carotenoid production. Methods of introducing expression vectors into plant tissue include direct gene transfer method such as microprojectile-mediated delivery, DNA injection, electroporation, and the like [See Gruber et al., infra; Miki et al., in *Methods in Plant Molecular Biology and Biotechnology,* Glick et al. eds., CRC Press, Boca Raton, Fla., pages 67–88 (1993); Klein et al., *Biotechnology* 10:268 (1992)]. Expression vectors are also introduced into plant tissues via direct infection or co-cultivation of plant tissue with *Agrobacterium tumefaciens* [See Horsch et al., *Science* 227:1229 (1985)]. Descriptions of *Agrobacterium* vector systems and methods for *Agrobacterium*-mediated gene transfer are provided by Gruber et al., "Vectors for Plant Transformation," in *Methods in Plant Molecular Biology and Biotechnology,* Glick et al. (eds.), pages 89–119 (CRC Press, 1993), Miki et al., supra, and Moloney et al., *Plant Cell Reports* 8:238 (1989).

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

The invention claimed is:

1. *Tagetes erecta* flower petals, leaves or both flower petals and leaves that contain zeaxanthin pigment and β-carotene pigment and are substantially free of lutein, and wherein the zeaxanthin pigment plus the β-carotene pigment together constitute at least about one-half of the total carotenoid pigments present and wherein the xanthophylls pigments are assayed as alcohols, said flower petals, leaves, or both flower petals and leaves being from a plant that is a chemically-induced mutant or a hybrid thereof.

2. The *Tagetes erecta* flower petals, leaves or both flower petals and leaves according to claim 1, wherein zeaxanthin pigment and β-carotene pigment together constitute about 60 to about 95 weight percent of the extractable carotenoid pigments present in petals, leaves or both flower petals and leaves of a contemplated plant, wherein xanthophylls are assayed as alcohols.

3. The *Tagetes erecta* flower petals, leaves or both flower petals and leaves according to claim 1, wherein β-carotene pigment constitutes about 5 to about 80 weight percent of the carotenoid pigments present in petals, leaves or both flower petals and leaves of a contemplated plant.

4. *Tagetes erecta* flower petals that contain zeaxanthin pigment esters and are substantially free of esters of both neoxanthin pigment and violaxanthin pigment, and wherein zeaxanthin pigment constitutes at least about one-half of the extractable carotenoids, wherein xanthophylls are assayed as alcohols, said flower petals being from a plant that is a chemically-induced mutant or a hybrid thereof.

5. A *Tagetes erecta* plant, or a regenerable portion thereof, whose flower petals contain zeaxanthin pigment esters and are substantially free of esters of both neoxanthin pigment and violaxanthin pigment, and wherein zeaxanthin pigment constitutes at least about one-half of the extractable carotenoids, wherein xanthophylls are assayed as alcohols, said plant being a chemically-induced mutant or a hybrid thereof.

6. Pollen of the *Tagetes erecta* plant of claim 5.

7. An ovule of the *Tagetes erecta* plant of claim 5.

8. Seed that on planting in a suitable environment and growth to maturity yields a *Tagetes erecta* plant according to claim 5.

9. The *Tagetes erecta* flower petals according to claim 1.

10. The *Tagetes erecta* flower petals according to claim 1 that are present in comminuted form.

11. The *Tagetes erecta* flower petals according to claim 1 that are from a hybrid.

12. The *Tagetes erecta* plant or a regenerable portion thereof according to claim 1, wherein the regenerable portion is cells selected from the group consisting of embryos, meristems, pollen, leaves, anthers, roots, root tips, and flowers, or protoplasts or callus derived therefrom.

13. *Tagetes erecta* flower petals, leaves, or both flower petals and leaves that contain zeaxanthin pigment and β-carotene pigment and are substantially free of lutein, and wherein the zeaxanthin pigment plus the β-carotene pigment together constitute at least about one- half of the total carotenoid pigments present and wherein the xanthophylls are assayed as alcohols, said flower petals, leaves, or both flower petals and leaves being from a plant that is an ionizing radiation-induced mutant or a hybrid thereof.

14. The *Tagetes erecta* flower petals, leaves or both flower petals and leaves according to claim 13, wherein zeaxanthin pigment and β-carotene pigment together constitute about 60 to about 95 weight percent of the extractable carotenoid pigments present in petals, leaves or both flower petals and leaves of a contemplated plant, wherein xanthophylls are assayed as alcohols.

15. The *Tagetes erecta* flower petals, leaves or both flower petals and leaves according to claim 13, wherein β-carotene pigment constitutes about 5 to about 80 weight percent of the carotenoid pigments present in petals, leaves or both flower petals and leaves of a contemplated plant.

16. *Tagetes erecta* flower petals that contain zeaxanthin pigment esters and are substantially free of esters of both neoxanthin pigment and violaxanthin pigment, and wherein zeaxanthin pigment constitutes at least about one-half of the extractable carotenoids, wherein xanthophylls are assayed as alcohols, said flower petals being from a plant that is an ionizing radiation-induced mutant or a hybrid thereof.

17. A *Tagetes erecta* plant, or a regenerable portion thereof, whose flower petals contain zeaxanthin pigment esters and are substantially free of esters of both neoxanthin pigment and violaxanthin pigment, and wherein zeaxanthin pigment constitutes at least about one-half of the extractable carotenoids, wherein xanthophylls are assayed as alcohols, said plant being an ionizing radiation-induced mutant or a hybrid thereof.

18. Pollen of the *Tagetes erecta* plant of claim 17.

19. An ovule of the *Tagetes erecta* plant of claim 17.

20. Seed that on planting in a suitable environment and growth to maturity yields a *Tagetes erecta* plant according to claim 17.

21. The flower petals of a *Tagetes erecta* plant according to claim 17.

22. The *Tagetes erecta* flower petals according to claim 21 that are present in comminuted form.

23. The *Tagetes erecta* flower petals according to claim 21 that are from a hybrid.

24. The *Tagetes erecta* plant or a regenerable portion thereof according to claim 17, wherein the regenerable portion is cells selected from the group consisting of embryos, meristems, pollen, leaves, anthers, roots, root tips, and flowers, or protoplasts or callus derived therefrom.

25. A food additive comprised of *Tagetes erecta* flower petals dry or native hydrated form as plucked from a flower head form that contain one or more of a zeaxanthin pigment and β-carotene pigment and are substantially free of lutein, and wherein the zeaxanthin pigment plus the β-carotene pigment together constitute at least about one-half of the total carotenoid pigments present and wherein the xanthophylls are assayed as alcohols, said flower petals being from a plant that is a chemically-induced mutant or a hybrid thereof.

26. The food additive according to claim 25, wherein said petals are substantially whole.

27. The food additive according to claim 25, wherein said petals are comminuted.

28. The food additive according to claim 25, wherein said petals are dried.

29. The food additive according to claim 25 that comprises dried, finely comminuted *Tagetes erecta* petals.

30. A food additive comprised of *Tagetes erecta* flower petals dry or native hydrated form as plucked from a flower head form that contain one or more of a zeaxanthin pigment and β-carotene pigment and are substantially free of lutein, and wherein the zeaxanthin pigment plus the β-carotene pigment together constitute at least about one-half of the total carotenoid pigments present and wherein the xanthophylls are assayed as alcohols, said flower petals being from a plant being an ionizing radiation-induced mutant or a hybrid thereof.

31. The food additive according to claim 30, wherein said petals are substantially whole.

32. The food additive according to claim 30, wherein said petals are comminuted.

33. The food additive according to claim 30, wherein said petals are dried.

34. The food additive according to claim 30, that comprises dried, finely comminuted *Tagetes erecta* petals.

\* \* \* \* \*